(12) United States Patent
Uribe-Romo et al.

(10) Patent No.: US 11,952,393 B1
(45) Date of Patent: Apr. 9, 2024

(54) MECHANICALLY SHAPED 2-DIMENSIONAL COVALENT ORGANIC FRAMEWORKS

(71) Applicant: UNIVERSITY OF CENTRAL FLORIDA RESEARCH FOUNDATION, INC., Orlando, FL (US)

(72) Inventors: Fernando Javier Uribe-Romo, Orlando, FL (US); Demetrius Vazquez-Molina, Orlando, FL (US); James K. Harper, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 0 days.

(21) Appl. No.: 17/970,831

(22) Filed: Oct. 21, 2022

Related U.S. Application Data

(62) Division of application No. 16/317,729, filed as application No. PCT/US2017/041705 on Jul. 12, 2017, now Pat. No. 11,512,099.

(Continued)

(51) Int. Cl.
*C07F 5/04* (2006.01)
*C07C 221/00* (2006.01)
(Continued)

(52) U.S. Cl.
CPC .............. *C07F 5/04* (2013.01); *C07C 221/00* (2013.01); *C07F 5/05* (2013.01); *H01M 4/043* (2013.01);
(Continued)

(58) Field of Classification Search
CPC . C07F 5/04; C07F 5/05; C07C 221/00; C07C 2601/14; H01M 4/043;
(Continued)

(56) References Cited

U.S. PATENT DOCUMENTS

| 8,088,356 B2 * | 1/2012 | Kang | ..................... B01J 20/226 |
| | | | 502/526 |
| 11,512,099 B2 | 11/2022 | Uribe-Romo et al. | |

FOREIGN PATENT DOCUMENTS

| KR | 1020160034183 A1 * | 3/2016 |
| WO | 2014203283 A4 | 12/2014 |
| WO | 2016055228 A1 | 4/2016 |

OTHER PUBLICATIONS

Doonan et al., Exceptional ammonia uptake by a covalent organic framework, 2010, Nature Chem., 2, 235-238 (Year: 2010).*

(Continued)

*Primary Examiner* — Daniel S Gatewood
(74) *Attorney, Agent, or Firm* — Timothy H. Van Dyke; WOLTER, VAN DYKE, DAVIS, PLLC

(57) ABSTRACT

Covalent organic frameworks (COFs) usually crystallize as insoluble powders and their processing for suitable devices has been thought to be limited. Here, it is demonstrated that COFs can be mechanically pressed into shaped objects having anisotropic ordering with preferred orientation between the hk0 and 00l crystallographic planes. Pellets prepared from bulk COF powders impregnated with LiClO$_4$ displayed room temperature conductivity up to 0.26 mS cm$^{-1}$ and stability up to 10.0 V (vs. Li$^+$/Li$^0$). This outcome portends use of COFs as solid-state electrolytes in batteries.

5 Claims, 11 Drawing Sheets

Related U.S. Application Data

(60) Provisional application No. 62/361,139, filed on Jul. 12, 2016.

(51) Int. Cl.
| | |
|---|---|
| *C07F 5/05* | (2006.01) |
| *H01M 4/04* | (2006.01) |
| *H01M 4/1397* | (2010.01) |
| *H01M 4/60* | (2006.01) |
| *H01M 10/0525* | (2010.01) |
| *H01M 10/056* | (2010.01) |
| *H01M 10/0564* | (2010.01) |

(52) U.S. Cl.
CPC ..... *H01M 10/056* (2013.01); *H01M 10/0564* (2013.01); *C07C 2601/14* (2017.05); *H01M 4/1397* (2013.01); *H01M 4/60* (2013.01); *H01M 10/0525* (2013.01)

(58) Field of Classification Search
CPC ........... H01M 10/056; H01M 10/0564; H01M 4/1397; H01M 4/60; H01M 10/0525
See application file for complete search history.

(56) References Cited

OTHER PUBLICATIONS

Xu, Fei et al., "Electrochemically active, crystalline, mesoporous covalent organic frameworks on carbon nanotubes for synergistic lithium-ion battery energy storage", Scientific Reports 2015, vol. 5, 8225-8230. (Year: 2015).*

International Search Report in International Application Serial No. PCT/US2017/041705, dated Nov. 22, 2017.

Written Opinion in International Application No. PCT/US2017/041705, dated Nov. 22, 2017.

Bachman, John Christopher, et al., "Inorganic Solid-State Electrolytes for Lithium Batteries: Mechanisms and Properties Governing Ion Conduction," Chemical Reviews, 2016, 116, pp. 140-162.

Bandaru, Nirup, et al., "Effect of Pressure and Temperature on Structural Stability of MoS2," The Journal of Physical Chemistry, 2014, 118, pp. 3230-3235.

Bunck, David N., et al., "Bulk Synthesis of Exfoliated Two-Dimensional Polymers Using Hydrazone-Linked Covalent Organic Frameworks," Journal of the American Chemical Society, 2013, 135, pp. 14952-14955.

Chandra, Suman, et al., "Chemically Stable Multilayered Covalent Organic Nanosheets from Covalent Organic Frameworks via Mechanical Delamination," Journal of the American Chemical Society, 2013, 135, pp. 17853-17861.

Chandra, Suman, et al., "Phosphoric Acid Loaded Azo (-N=N-) Based Covalent Organic Framework for Proton Conduction," Journal of the American Chemical Society, 2014, 136, pp. 6570-6573.

Chen, Chih-Ping, et al., "Highly Thermal Stable and Efficient Organic Photovoltaic Cells with Crosslinked Networks Appending Open-Cage Fullerenes as Additives," Advanced Functional Materials, 2015, 25, pp. 207-213.

Chong, Jonathan H. et al., "Highly Stable Keto-Enamine Salicylideneanilines", American Chemical Society, Org. Lett., 2003, vol. 5, No. 21, pp. 3823-3826.

Colson, John W. et al., "Oriented 2D Covalent Organic Framework Thin Films on Single-Layer Graphene", Science, 2011, vol. 332, pp. 228-231.

Colson, John W. et al., "Rationally synthesized two-dimensional polymers", Nature Chemistry, 2013, vol. 5, pp. 453-465.

Colson, John W. et al., "Patterned Growth of Oriented 2D Covalent Organic Framework Thin Films on Single-Layer Graphene", Journal of Polymer Science, Polymer Chemistry, 2015, vol. 53, pp. 378-384.

Cote, Adrien P. et al., "Porous, Crystalline, Covalent Organic Frameworks", Science, Nov. 2005, vol. 310, pp. 1166-1170.

Deblase, Catherine R. et al., "β-Ketoenamine-Linked Covalent Organic Frameworks Capable of Pseudocapacitive Energy Storage", Journal American Chemical Society, 2013, vol. 135, pp. 16821-16824.

Deblase, Catherine R. et al., "Rapid and Efficient Redox Processes within 2D Covalent Organic Framework Thin Films", American Chemical Society NANO, 2015, vol. 9, No. 3, pp. 3178-3183.

Dogru, Mirjam et al., "A Photoconductive Thienothiophene-Based Covalent Organic Framework Showing Charge Transfer Towards Included Fullerene", Angew. Chem. Int. Ed., 2013, vol. 52, pp. 2920-2924.

Dogru, Mirjam et al., "On the road towards electroactive covalent organic frameworks", Chem. Commun., 2014, vol. 50, pp. 5531-5546.

Doonan, Christian J. et al., "Exceptional ammonia uptake by a covalent organic framework", Nature Chemistry, Mar. 2010, vol. 20 pp. 235-238.

Du, Ya et al., "Ionic Covalent Organic Frameworks with Spiroborate Linkage", Angew. Chem. Int. Ed., 2016, vol. 55, pp. 1737 -1741.

El-Kadeir, Hani M. et al., "Designed Synthesis of 3D Covalent Organic Frameworks", Science, Apr. 2007, vol. 316, pp. 268-272.

Fung, B.M. et al. "An Improved Broadband Decoupling Sequence for Liquid Crystals and Solids", Journal of Magnetic Resonance, 2000, vol. 142, pp. 97-101.

Goodenough, John B. et al., "Challenges for Rechargeable Li Batteries", Chem. Mater., 2010, vol. 22, pp. 587-603.

Ivanov, A.V. et al., "New phthalocyanine complexes based on 4,5isopropylidenedioxyphthalonitrile", Russian Chemical Bulletin, Jul. 2003, vol. 52, No. 7, pp. 1562-1566.

Kalhoff, Julian et al., "Safer Electrolytes for Lithium-Ion Batteries: State of the Art and Perspectives", ChemSusChem, 2015, vol. 8, pp. 2154-2175.

Kamaya, Noriaki et al., "A lithium superionic conductor", Nature Materials, Sep. 2011, vol. 10, pp. 682-686.

Kandambeth, Sharath et al., "Construction of Crystalline 2D Covalent Organic Frameworks with Remarkable Chemical (Acid/Base) Stability via a Combined Reversible and Irreversible Route", J. Am. Chem. Soc. 2012, vol. 134, p. 19524-19527.

Kuhn, Pierre et al, "Porous, Covalent Triazine-Based Frameworks Prepared by Ionothermal Synthesis", Angew. Chem. Int. Ed. 2008, vol. 47, pp. 3450-3453.

Ma, Heping et al., "Cationic Covalent Organic Frameworks: A Simple Platform of Anionic Exchange for Porosity Tuning and Proton Conduction", J. Am. Chem. Soc. 2016, vol. 138, pp. 5897-5903.

Manson, James E., "Preferred Orientation of Platelets in X-Ray Diffractometer Powder Samples", Journal of Applied Physics, Oct. 1955, vol. 26, No. 10, pp. 1254-1256.

Morimoto, Koji et al, "Oxidative Trimerization of Catechol to Hexahydroxytriphenylene", Eur. J. Org. Chem. 2013, pp. 1659-1662.

Sakamoto, Junji et al., "Two-Dimensional Polymers: Just a Dream of Synthetic Chemists?", Angew. Chem. Int. Ed. 2009, vol. 48, pp. 1030-1069.

Shinde, D. B. et al., "A mechanochemically synthesized covalent organic framework as a proton-conducting solid electrolyte", J. Mater. Chem. A, 2016, vol. 4, pp. 2682-2690.

Spitler, Eric L. et al., "A 2D Covalent Organic Framework with 4.7-nm Pores and Insight into Its Interlayer Stacking", J. Am. Chem. Soc. 2011, vol. 133, pp. 19416-19421.

Spitler, Eric L. et al., "Lattice Expansion of Highly Oriented 2D Phthalocyanine Covalent Organic Framework Films", Angew. Chem. Int. Ed. 2012, vol. 51, pp. 2623-2627.

Vanhumbeck, Jeffrey F. et al., "Tetraarylborate polymer networks as single-ion conducting solid electrolytes", Chem. Sci., 2015, vol. 6, pp. 5499-5505.

Vaudin, Mark D., "Crystallographic Texture in Ceramics and Metals", J. Res. Natl. Inst. Stand. Technol. 2001, vol. 106, pp. 1063-1069.

Vazquez-Molina, Demetrius A et al., "Mechanically Shaped Two-Dimensional Covalent Organic Frameworks Reveal Crystallographic Alignment and Fast Li-Ion Conductivity", J. Am. Chem. Soc. 2016, vol. 138, pp. 9767-9770.

(56) References Cited

OTHER PUBLICATIONS

Waller, Peter J., et al., "Chemistry of Covalent Organic Frameworks", Acc. Chem. Res. 2015, vol. 48, pp. 3053-3063.

Wan, Shun et al., "Covalent Organic Frameworks with High Charge Carrier Mobility", Chem. Mater. 2011, vol. 23, pp. 4094-4097.

Wiers, Brian M. et al., "A Solid Lithium Electrolyte via Addition of Lithium Isopropoxide to a MetalOrganic Framework with Open Metal Sites", J. Am. Chem. Soc. 2011, vol. 133, pp. 14522-14525.

Xu, Fei et al., "Electrochemically active, crystalline, mesoporous covalent organic frameworks on carbon nanotubes for synergistic lithium-ion battery energy storage", Scientific Reports 2015, vol. 5, 8225-8230.

Xu, Hong et al., "Proton conduction in crystalline and porous covalent organic frameworks", Nature Materials, Jul. 2016, VOl. 15, pp. 722-727.

Yang, Hui et al., "High Conductive Two-Dimensional Covalent Organic Framework for Lithium Storage with Large Capacity", ACS Appl. Mater. Interfaces 2016, vol. 8, pp. 5366-5375.

Zhao, You Xiang et al., "X-ray diffraction data for graphite to 20 Gpa", The American Physical Society, 1989, vol. 40, No. 2, pp. 993-997.

Vazquez-Molina, Demetrius A. et al., "Mechanically shaped two-dimensional covalent organic frameworks reveal Crystallographic alignment and fast Li-Ion conductivity", JACS, 2016, vol. 138, pp. 9767-9770.

\* cited by examiner

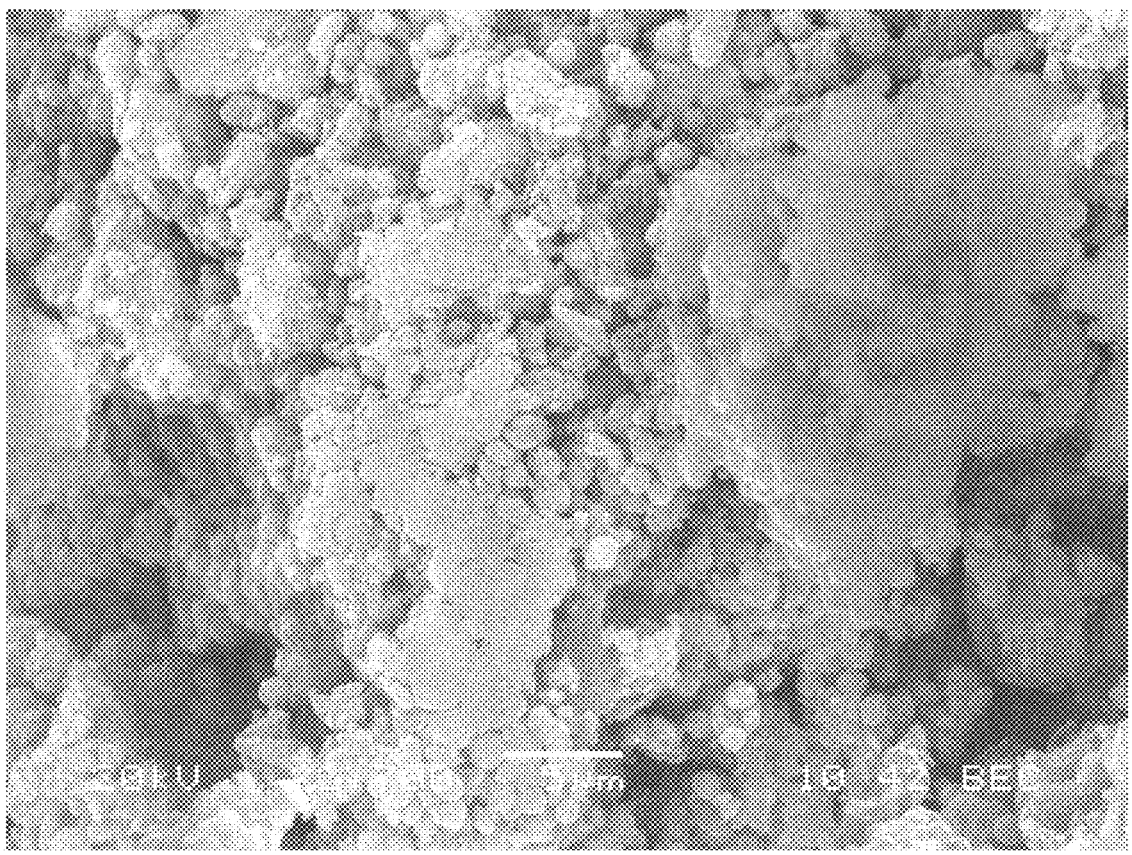
FIG. 5
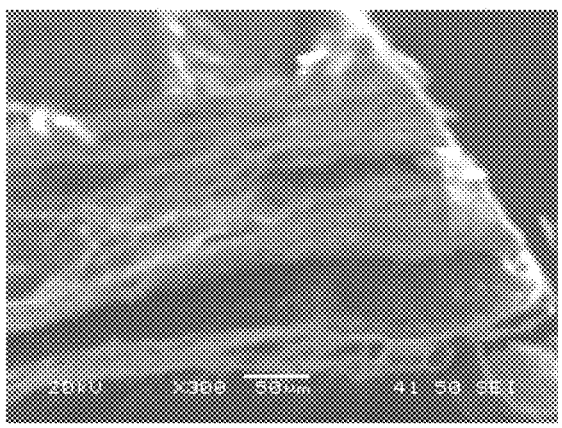 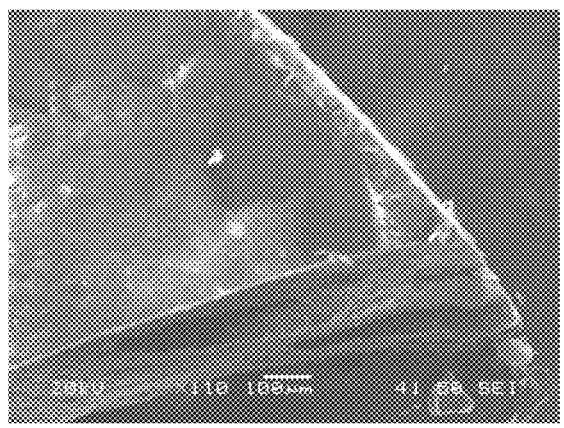
FIG. 6A    FIG. 6B

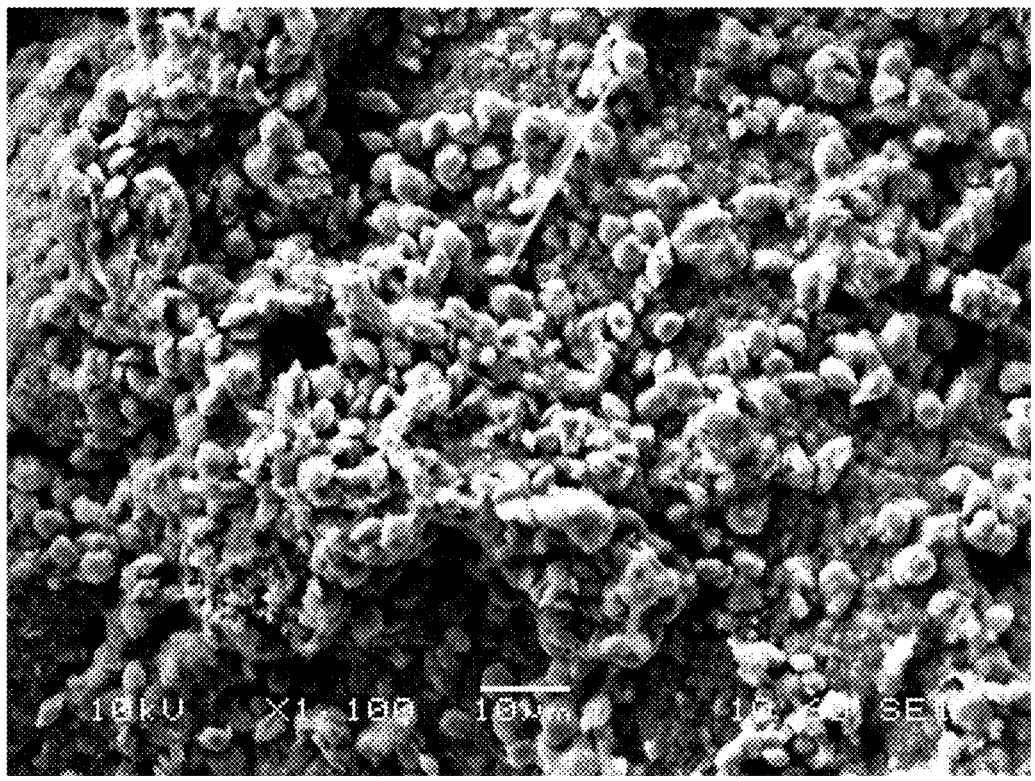
FIG. 11
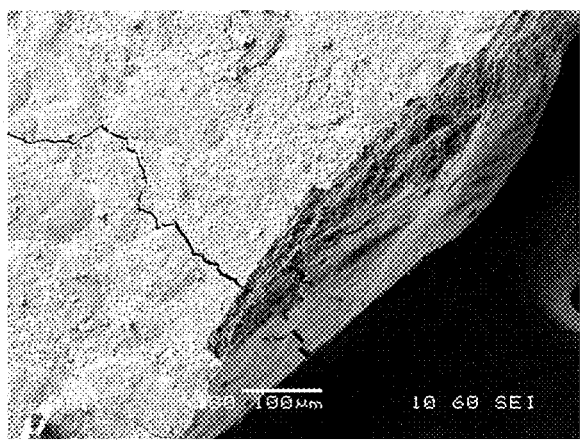 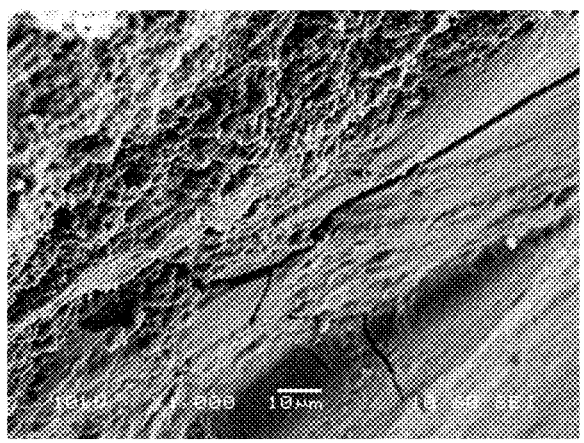
FIG. 12A　　　　　　　　　　　　　　　FIG. 12B

MECHANICALLY SHAPED 2-DIMENSIONAL COVALENT ORGANIC FRAMEWORKS

ACKNOWLEDGEMENT OF GOVERNMENT SUPPORT

This invention was made with government support under Grant No. CHE1455159 awarded by the National Science Foundation. The government has certain rights in the invention.

BACKGROUND

Covalent organic frameworks (COFs) (Côté, A. P., et al., Science 2005, 310, 1166-1170; Colson, J. W., et al., Nature Chem. 2013, 5, 453-465; Waller, P. J., et al., Acc. Chem. Res. 2015, 48, 3053-3063; Thote, J et al., International Union of Crystallography Journal (IUCrJ) Volume 3 (6), 2016, 402-407) have become of increasing interest in materials chemistry due to their potential application in photovoltaic (Wan, S., et al., Chem. Mater. 2011, 23, 4094-4097; Dogru, M., et al., Angew. Chem. Int. Ed. 2013, 52, 2920-2924; Dogru, M., et al., Chem. Commun. 2014, 50, 5531-5546; Chen, C.-P., et al., Adv. Funct. Mater. 2015, 25, 207-213), electrochemical devices (DeBlase, C. R., et al., J. Am. Chem. Soc. 2013, 135, 16821-16824; DeBlase, C. R., et al., ACS Nano 2015, 9, 3178-3183; Yang, H, et al., ACS Appl. Mater. Interfaces 2016, 8, 5366-5375; Xu, F., et al., Scientific. Rep. 2015, 5, 8225), and gas storage (Doonan, C. J., et al., Nature Chem. 2010, 2, 235-238). 2-Dimensional (2D) COFs typically crystallize as stacked sheets that precipitate as insoluble powders, and are assumed to be unprocessable (Sakamoto, J., et al., Angew. Chem. Int. Ed. 2009, 48, 1030-1069). The cylindrical shape, tunable narrow size of the pore system, and chemical stability of 2D COFs, make them ideal candidates for applications where unidirectional mass transport is desired, e.g. the transport of ions in an electric field.

Thin films of 2D COFs have been prepared by Dichtel et al. and Banerjee et al., by either addition of flat substrates to the crystallizing mixture (Colson, J. W., et al., Science 2011, 332, 228-231; Spitler, E. L., et al., J. Am. Chem. Soc. 2011, 133, 19416-19421; Spitler, E. L., et al., Angew. Chem. Int. Ed. 2012, 51, 2623-2627), or mechanical delamination of powders (Chandra, S., et al. J. Am. Chem. Soc. 2013, 135, 17853-17861; Bunck, D. N., et al., J. Am. Chem. Soc. 2013, 135, 14952-14955), obtaining highly aligned samples with thicknesses up to 200 nm. However, the preparation of macroscopic COF samples with crystallographic alignment for large devices has not been realized. What are thus needed are meso- and macroscopic COF samples, with anisotropic properties, and methods to prepare such materials. The compositions and preparation methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to methods of processing a covalent organic framework that comprise applying pressure to the covalent organic framework along a uniaxial direction. Covalent organic frameworks prepared by the disclosed methods and devices such as batteries comprising such materials are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 1A shows a unit cell of COF-5 illustrating the stacking and anisotropic orientations of crystalline planes (e.g., orthogonallity between $d_{hk0}$ and $d_{00l}$ planes normal vectors). FIG. 1B is a depiction of a COF pellet oriented parallel to the optical axis. FIG. 1C is a powder x-ray diffraction (PXRD) of a COF-5 pellet in parallel mode at varying uniaxial pressure. FIG. 1D shows a COF pellet oriented perpendicular to the optical axis. FIG. 1E is a PXRD of a COF-5 pellet in perpendicular mode at varying uniaxial pressure. The 001 peak is shown inset and it is expanded 50 times for clarity. $d^T$ corresponds to the optical axis normal vector, and $d_{hkl}$ to the hkl plane normal vector.

FIG. 5 is a micrograph of COF-5 powder showing the agglomerated morphology of the microcrystalline powder. Scale is indicated.

FIGS. 6A and 6B are plan-view micrographs of COF-5 pellet showing the sheet-like morphology of the crystallographically oriented pellet. Scale is indicated.

FIG. 11 is a micrograph of ZnPc-BBA COF powder evidencing agglomerate morphology of the microcrystalline powder. Scale is indicated.

FIGS. 12A and 12B are micrograph of ZnPc-BBA COF pellet showing the change in morphology of the crystallographically oriented pellet. Scale is indicated

DETAILED DESCRIPTION

Figures 1A, 1B, 1C, 1D, 1E:
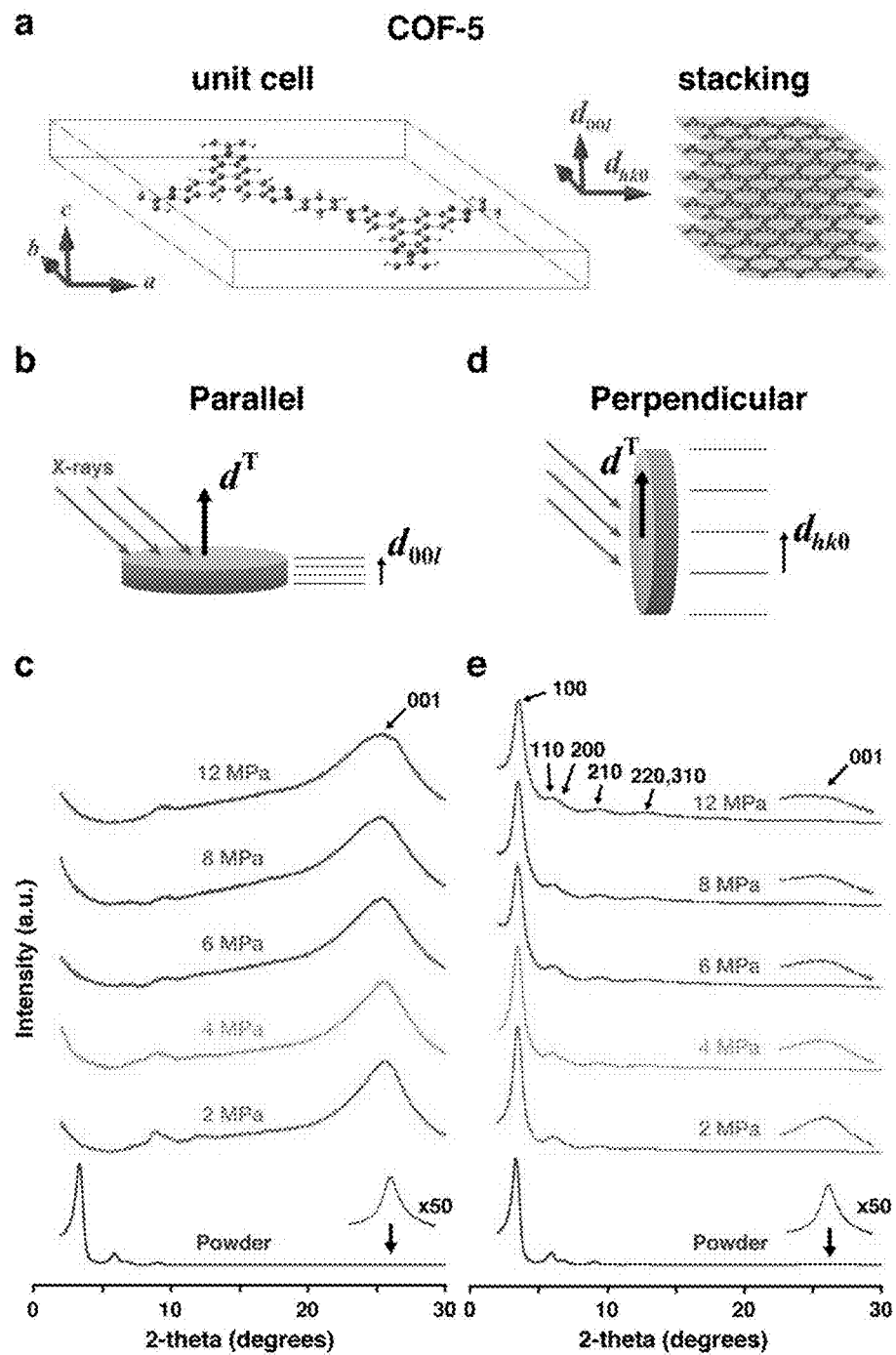
FIGS. 1A through 1E.

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

As used herein, the term "composition" is intended to encompass a product comprising the specified ingredients in the specified amounts, as well as any product which results, directly or indirectly, from combination of the specified ingredients in the specified amounts.

The term "uniaxial" means along the optical axis of a crystal, e.g., a hexagonal, trigonal, tetragonal system, rhombohedral, orthorhombic, or monoclinic symmetry.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

Reference will now be made in detail to specific aspects of the disclosed materials, compounds, compositions, articles, and methods, examples of which are illustrated in the accompanying Examples and Figures. The examples below are intended to further illustrate certain aspects of the methods and compounds described herein, and are not intended to limit the scope of the claims.

Covalent Organic Frameworks (COF)

Covalent Organic Frameworks (COFs) are three dimensional crystalline materials prepared by linking lighter elements (e.g., B, C, N, O) via covalent bonds in a periodic manner. COFs are typically synthesized and subsequently crystallized by means of reversible condensation reactions/covalent bond formation reactions such as boronic acid trimerisation, boronate ester formation, borazine formation, and Schiff base reaction (Thote, J., et al. International Union of Crystallography Journal (IUCrJ) Volume 3 (6), 2016, 402-407; https://doi.org/10.1107/s2052252516013762 (2016)). Structurally, COFs are closely related to metal-organic frameworks (MOFs), where coordination bonds link metal ions and organic struts. Metal-organic frameworks (MOFs) can facilitate ionic conduction by accommodating guest molecules, such as water and imidazole, in well-defined pores or integrating functional acidic groups onto the channel walls. Although COFs have shown excellent promise as semiconductive device, sensors, in gas storage and in separation, ionic conductivity ($Li^+$, $Na^+$, $Mg^{+2}$, $Al^{+3}$) in COFs are still unprecedented.

The 2-D variants of COFs crystallize into layered structures containing stacked aromatic subunits ideal for interlayer exciton and charge transport. 2-D COFs exhibit several desirable and unique features. The length and relative orientation of their linking groups determine the lattice structure, in contrast to the unpredictable packing of traditional organic semiconductors. Also, their permanent porosity provides a continuous, high surface-area interface for additional functionalization. Moreover, 2-D variants of COFs contain pores with cylindrical and unidirectional shape. The pore of 2-D COFs can be decorated with functional groups that are chemically attached to the building blocks before the COF synthesis.

Disclosed herein are 2D COF powders that have been mechanically pressed into pellets with high degree of crystallographic anisotropy. The crystallographic and ionic transport features of these materials are also disclosed. Further disclosed are methods that can be applied to different COFs with diverse functionalities (e.g., boronate, boroxine, β-ketoenamine, triazine) and symmetries (e.g., hexagonal, trigonal, tetragonal, rhombohedral, orthorhombic, or monoclinic symmetry), and used in the preparation of COFs for large devices; in particular, as solid-state fast-ion conductors for Li-ion. Further, highly aligned porous 2D COFs can be specifically tailored to conduct Li-ion at ultrafast rates for their use as electrolytes in all solid-state batteries.

In the disclosed methods, weak t-t interaction between the layers of the COF can allow for easy sliding under uniaxial mechanical stress allowing an anisotropic packing of the crystallites, in a similar fashion to weakly bound layered materials such as graphite and $MoS_2$. In the disclosed examples, the archetypical COF-5 (Côté, A. P., et al., *Science* 2005, 310, 1166-1170), which packs in a hexagonal crystal system with two degrees of freedom: a=b, and c (FIG. 1A), where the covalently bound sheets lay along ab (FIG. 1A, green arrows) and stack along c (FIG. 1A, blue arrow) through π-π interactions. This hexagonal packing allows for two sets of Bragg planes: hk0 and 00l, which are orthogonal to each other, and are the signature for any anisotropy in the diffraction pattern. Bulk powders of the COF were prepared, and a typical powder X-ray diffraction (PXRD) pattern of the fully isotropic powder is shown in FIG. 1C and FIG. 1E (dark blue trace).

Pressure can be applied to the COF powders in a uniaxial direction. In certain examples, the pressure that is applied is at least 2 MPa, e.g., at least 4 MPa, 6 MPa, 8 MPa, 10 MPa, 12 MPa, or 14 MPa. In other examples, the pressure is 2 MPa, 3 MPa, 4 MPa, 5 MPa, 6 MPa, 7 MPa, 8 MPa, 9 MPa, 10 MPa, 11 MPa, 12 MPa, 13 MPa, 14 MPa, or 15 MPa, wherein any of the stated values can form an upper or lower endpoint of a range.

Upon pressing samples of the COF powder into pellets using a uniaxial hydraulic press, an apparent loss of crystallinity was observed when the diffractogram was measured with the pellet resting on its round side parallel to the optical axis (FIG. 1B, hereafter parallel mode), which is also parallel to the uniaxial press, at increasing uniaxial pressure (FIG. 1C). Surprisingly, the broad diffraction peak at 260 2-theta, which corresponds to the 001 Bragg reflection, was predominantly observed, even when pressing the pellet up to 12 MPa. Turning the pellet 90°—resting on its edge—(FIG. 1D, hereafter perpendicular mode) resulted in a pattern that displayed the expected low angle hk0 peaks in COF-5 (FIG. 1E). Moreover, the intensity of the 001 peak decreased with increasing uniaxial pressure (FIG. 1E, inset). According to Bragg theory, in order to observe diffraction, the $d_{hkl}$ normal vector must be parallel to the optical axis normal vector, $d^T$ (FIG. 1B), in which for the isotropic powder, all the Bragg planes fulfill this condition. This is the case for the 00l planes (along c axis) in parallel mode, but not for the hk0 (along ab axis). If these hk0 planes are aligned perpendicular to $d^T$, they will not diffract. Similarly, when the pellet is aligned in perpendicular mode, the $d_{hkl}$ vector of the hk0 planes are now aligned with the $d^T$, and therefore able to diffract. Observations indicate that there is an anisotropic orientation induced by mechanical pressing, where the 00l planes are the only ones that fulfill the diffraction condition when the pellet is in parallel mode, and the hk0 planes when the pellet is in perpendicular mode. This behavior is pressing a 3-dimensional COF (COF-102) into a pellet, observing known in powder diffractometry as preferred orientation, and is observed intensely in large crystals with a very anisotropic crystallite shape (Manson, J. E., *J. Appl. Phys.* 1955, 26, 1254-1256) and in thin films (Vaudin M. D., *J. Res. Natl. Inst. Stand. Technol.* 2001, 106, 1063-1069). Thus, while the preferred orientation is commonly observed in crystals with plate or needle shape, in this invention anisotropy observed only after the pellet is pressed.

Figure 2:
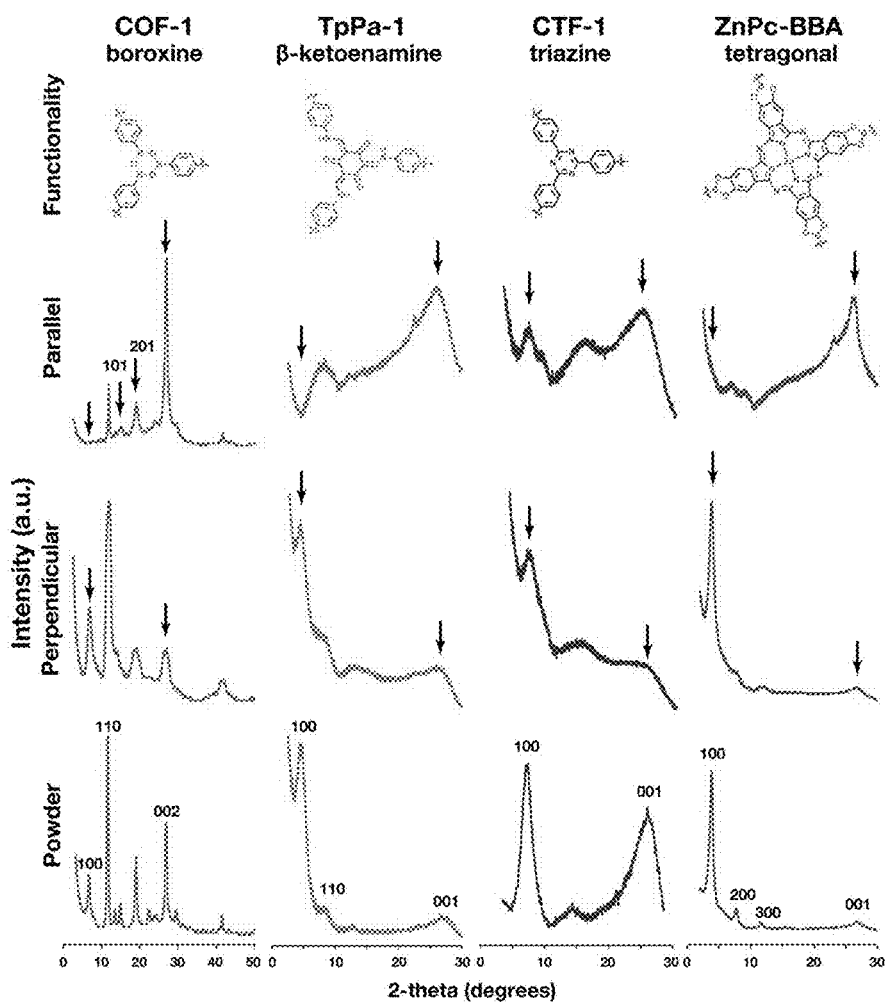
FIG. 2 shows PXRD patterns of COFs with multiple functionality (top) in powder (bottom) and pellets in both orientations (middle). Pellets pressed at 12 MPa (CTF-1 pressed at 15 MPa). The preferred orientation of the 100 and 001 (002 for COF-1) reflections is indicated with arrows.

This pressure induced crystallographic preferred orientation has been observed in other 2D materials that stack through van der Waals forces, but only in inorganic materials at very high pressures (Zhao, Y. X., et al., *Phys. Rev. B* 1989, 40, 993-997; Bandaru, N., et al., *J. Phys. Chem. C* 2014, 118, 3230-3235, Coudert, F-X, Chem. Mater., 2015, 27 (6), pp 1905-1916). Preferred orientation in COFs is a very attractive feature, because inducing alignment of the COF crystals will also result in the alignment of the cylindrical pores. This alignment will make COFs applicable where pore orientation is vital; for example, in the transport of charged species in electrochemical devices. This is a surprising discovery since theoretical studies of the stacking of 2D COFs predict offset stacked layers rather than perfectly eclipsed average structure derived from powder refinement (Bisbey, R. P. and Dichtel, W. R., ACS Cent. Sci., 2017, 3 (6), pp 533-543). While not wishing to be bound by theory, it is believed that this phenomenon is inherent of all layered 2D COFs; therefore, the effect of uniaxial pressing in other 2D COFs bulk powders with different functionality and crystal symmetry was explored. Powder samples of hexagonal COF-1 (boroxine) (Côté, A. P., et al., *Science* 2005, 310, 1166-1170), TpPa-1 COF (β-ketoenamine) (Kandambeth, S., et al., *J. Am. Chem. Soc.* 2012, 134, 19524-195270), CTF-1 (triazine) (Kuhn, P., et al., *Angew. Chem. Int. Ed.* 2008, 47, 3450-3453), and tetragonal ZnPc-BBA COF (boronate) (Colson, J. W., et al., *J. Polym. Sci. Part A: Polym. Chem.* 2015, 53, 378-384) were pressed into pellets and observed the similar crystallographic behavior as in COF-5. All four COFs displayed the preferred orientation (FIG. 2). When the pellets were oriented in parallel mode, all the COFs displayed an intensity increase along the 001 reflection (002 for COF-1) and attenuation of the 100 peaks. In the case of COF-1, some residual intensity was observed in the 110 reflections; however, the intensity of the 002 peak is significantly enhanced and even some non-orthogonal h0l reflections remain (such as 101 and 201), consistent with their alignment with respect to the optical axis. In the perpendicular mode, all COFs displayed the corresponding hk0 peaks with attenuation of the 00l reflections. Once again, COF-1 displayed another interesting feature, an obvious difference in peak width. This peak width is a result of anisotropic crystallite size and strain, as discussed below. A negative control was performed by complete loss of crystallinity in either pellet orientation suggesting that only 2D COFs exhibit this property.

Figure 3A:
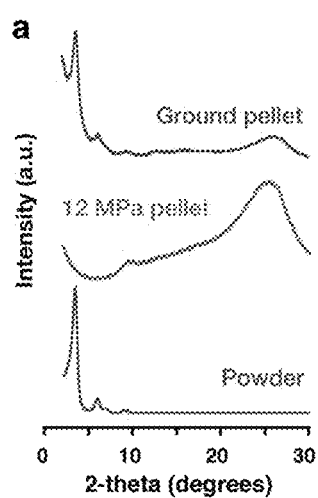
FIG. 3A is a PXRD of COF-5 as powder before mechanical pressing (purple), as pellet in parallel mode (red), and after grinding of the pellet (blue), indicating the crystalline stability after mechanical stress.
Figure 3B:
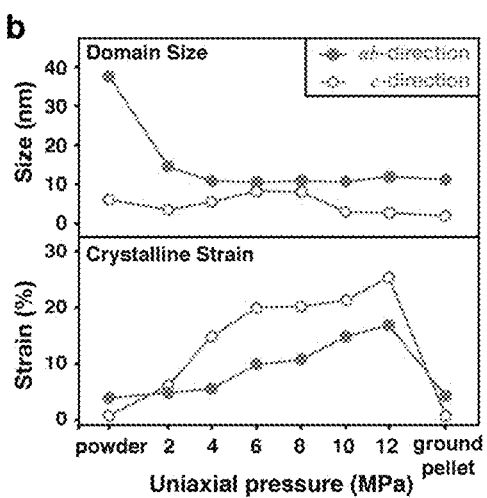
FIG. 3B shows crystalline domain size and strain of COF-5 at varying uniaxial pressures, as determined from line width analysis using Le Bail refinement evidencing the effects of the mechanical stress.

Grinding a pellet into a powder resulted in complete recovery of the diffraction peaks as in the isotropic powder (FIG. 3A), indicating the stability of the COF under mechanical stress. As could be noted in FIG. 1C and FIG. 1E, gradual broadening of the diffraction peaks was observed with increasing uniaxial pressure, and after regrinding the pellets. Le Bail refinement of the diffraction powders allowed the determination of crystalline domain size and strain present in the powder, pellets and ground pellet along the ab- and c-unit cell directions (FIG. 3B). Pressing the COF-5 powder into a pellet induces a decrease of the crystalline domain size by 75% but only along ab, and no significant change is observed along c. This decrease in size seems to be independent of the applied pressure and the domain size is preserved even after regrinding of the pellet pressed at 12 MPa. The most interesting feature is the change in crystalline strain. A gradual increase in strain is observed along both directions with increasing uniaxial pressure, up to ca. 25% along c at 12 MPa, induced from deviations in the interplanar distances of the sheets, as a consequence of the applied mechanical stress. This strain is then relieved when the pellet is ground back into a powder, and it is an interesting trait that could affect the mechanical properties and performance of 2D COFs in devices. The morphological changes of the COFs at the mesoscopic scale were also observed via Scanning Electron Microscopy (SEM) displaying a drastic change in sample morphology. The COF samples change their particle shape from globular agglomerates of COF crystallites in the powder form (FIG. 5), to highly anisotropic sheet-like features in the pellet (FIGS. 6A and 6B) in which the sheets are perpendicular to the direction of the press, supporting preferred orientation observed crystallographically.

The effect of the mass transfer within the pores of the compressed COFs was studied to provide insight into the alignment of the cylindrical pores, but more specifically ionic transfer, thus exploring the applicability of COFs as solid-state electrolytes for their use in safer and more efficient all-solid-state lithium-ion batteries (Kalhoff, J., et al., *ChemSusChem* 2015, 8, 2154-2175). COFs have been utilized as solid electrolytes for proton conduction (Chandra, S., et al., *J. Am. Chem. Soc.* 2014, 136, 6570-73; Shin-de, D. B., et al., *J. Mater. Chem. A* 2015, 4, 2682-2690; Ma, H., et al., *J. Am. Chem. Soc.* 2016, 138, 5897-5903; Xu, H., *Nature Mater.* 2016, DOI: 10.1038/nmat4611); however, there are only a few studies on conductivity of larger cations in organic frameworks. Powders of COF-5 and TpPa-1 COFs were immersed in 1 M LiClO$_4$/THF solutions for 48 h to allow impregnation of the lithium salt into the pores. Evaporation of excess solvent after removal from the lithium solution by filtration and thorough rinse provided dry COF powder that was pressed into pellets under 4 MPa uniaxial pressures. Electrochemical impedance spectroscopy (EIS) was performed on the pellets of COFs impregnated with LiClO$_4$, to study their use as solid state electrolytes for Li-ion batteries. In both cases a Nyquist behavior was observed (FIG. 4A), where the plot of the real component (Z) vs. the imaginary component (Z") of the complex impedance function displays a semicircular shape followed by a spike. The conductivity of the solid electrolyte can be determined from this plot where the resistance of the electrolyte is the real component of the impedance at high frequencies, resulting in ionic conductivities $\sigma$=0.26 mS cm$^{-1}$ and 0.15 mS cm$^{-1}$ for COF-5 (FIG. 4A) and TpPa-1, respectively, at room temperature. Pellets of non-impregnated COFs displayed no Nyquist behavior, evidencing the conductivity observed is due to LiClO$_4$ in the material. Variable temperature studies on the COF-5 pellet allowed the determination of the bulk activation energy for the ionic conductivity ($E_a$) using the linear Arrhenius plot (FIG. 4B), resulting in $E_a$=37±4 meV. The conductivity observed is within the recommended range for actual devices (Goodenough, J. B., et al., *Chem. Matter.* 2010, 22, 587-603), and competitive with other materials such as a spiroborate based COF (Du, Y., et al., *Angew. Chem. Int. Ed.* 2016, 55, 1737-1741), borate amorphous organic porous polymers (Van Humbeck, J. F., et al., *Chem. Sci.* 2015, 6, 5499-5505), LiGePS superionic conductors (Kamaya, N., et al., *Nature Mater.* 2011, 10, 682-686) and other inorganic materials (Wiers, B. M., et al., *J. Am. Chem. Soc.* 2011, 133, 14522-14525; Bachman, J. C, et al., *Chem. Rev.* 2016, 116, 140-162). It is noteworthy to mention that the activation energy of LiClO$_4$ impregnated COF-5 is six times smaller than the previously mentioned materials, which implies that the conductivity is less dependent on the temperature in the measured range.

The electrochemical stability of the LiClO$_4$ impregnated COF-5 pellet was measured in an asymmetric 2-electrode Li|LiClO$_4$ (COF-5)|steel cell utilizing cyclic voltammetry (CV). Besides a small amount of Li deposition/dissolution at negative potentials, the CV displays a featureless trace between −1.0 and 10. V, vs. Li$^+$/Li$^0$ for up to 100 cycles or more, surpassing the stability observed in the LiGePS ceramics (Kamaya, N., et al., *Nature Mater.* 2011, 10, 682-686). The high ionic conductivity, low temperature effect on conductivity, and high electrochemical stability makes crystallographically aligned COF-5 a competitive candidate for solid electrolytes in rechargeable Li-ion batteries.

Figures 4A, 4B, 4C, 4D:
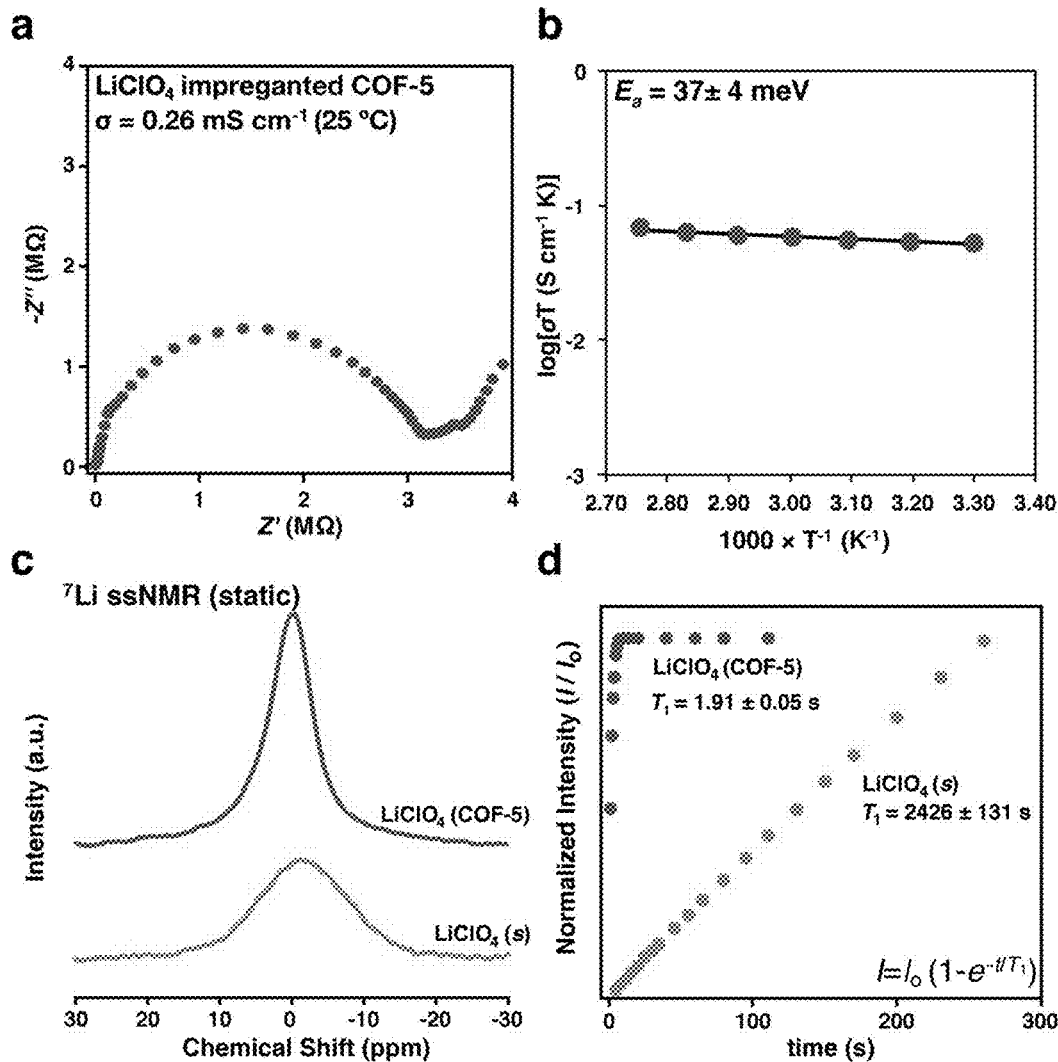
FIG. 4A is a graph of complex impedance function and FIG. 4B is an Arrhenius plot of COF-5 impregnated with $LiClO_4$, the conductivity at room temperature and activation energy are indicated.
FIG. 4C is a static $^7Li$ Solid State Nuclear magnetic resonance (ssNMR) spectra of COF-5 impregnated with $LiClO_4$ (purple), compared to pure crystalline $LiClO_4$ (green).
FIG. 4D is a saturation recovery plot from $^7Li$ ssNMR spectra (7 kHz, magic angle spinning) of COF-5 impregnated with $LiClO_4$ (purple) versus pure $LiClO_4$ (green). $T_1$ relaxation time constant in each material reveals the differences in the chemical environment, hence mobility of the $^7Li$-ions.
Figure 7:
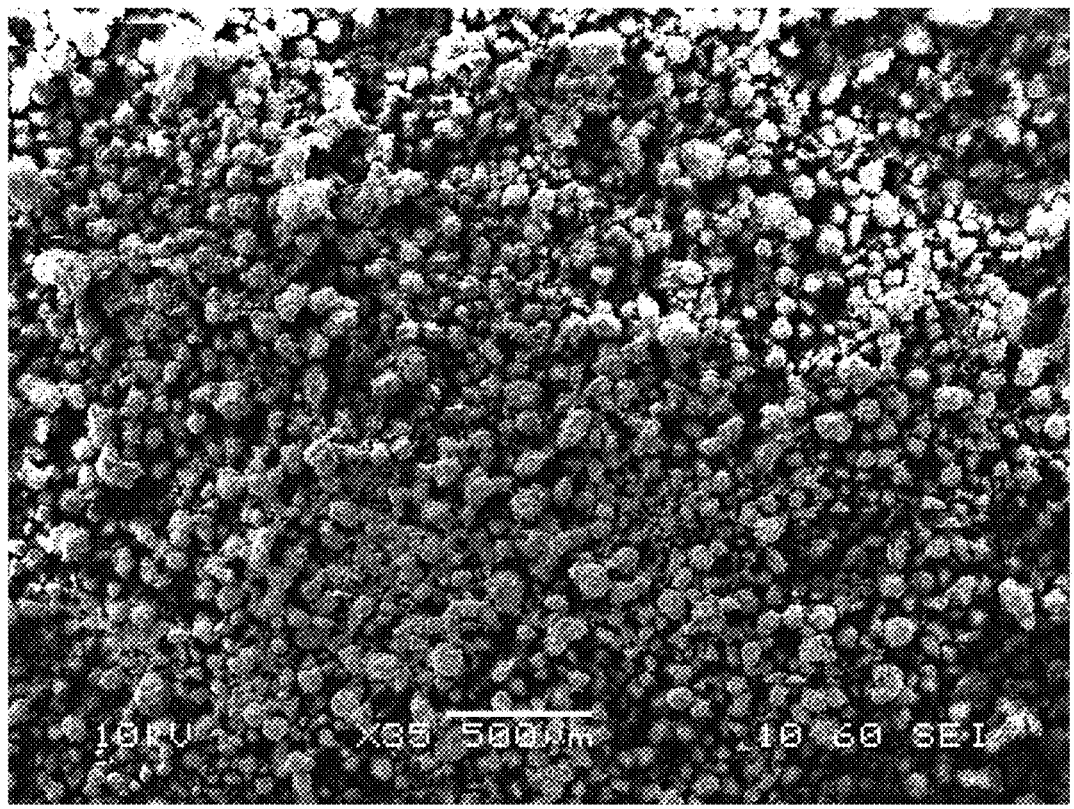
FIG. 7 is a micrograph of COF-1 powder showing the agglomerated morphology of the microcrystalline powder. Scale is indicated.
Figure 8A:
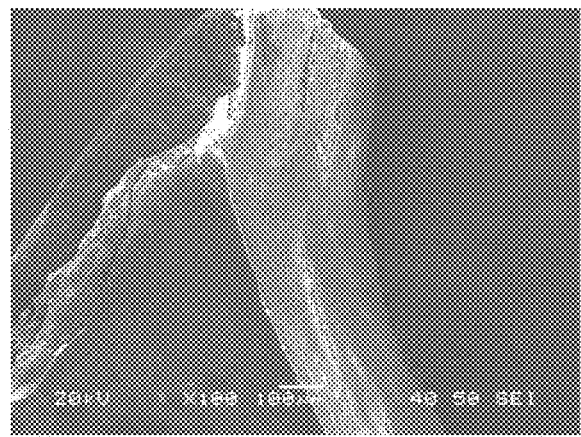
FIGS. 8A and 8B are micrographs of COF-1 pellet showing the change in morphology of the crystallographically oriented pellet. Scale is indicated.
Figure 8B:
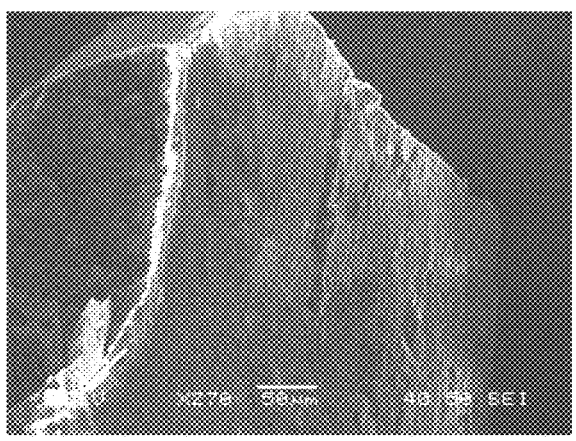
Figure 9:
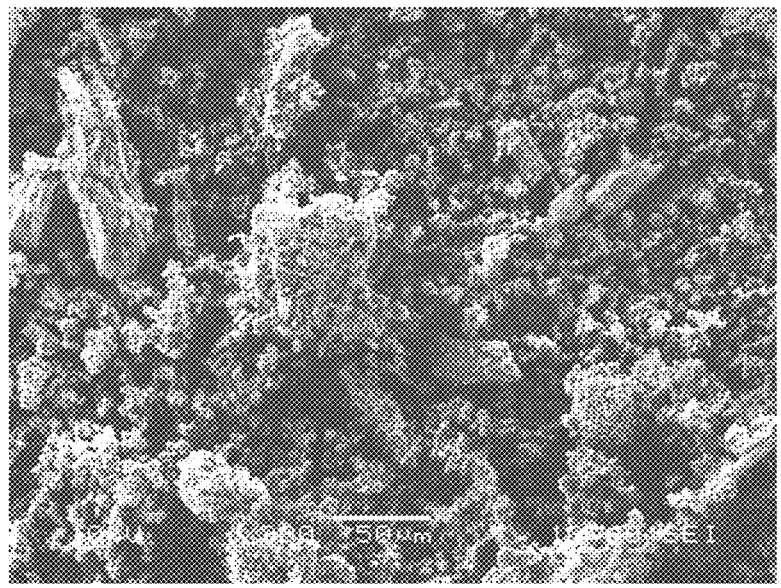
FIG. 9 is a micrograph of TpPa-1 powder showing the agglomerate morphology of the microcrystalline powder. Scale is indicated.
Figure 10:
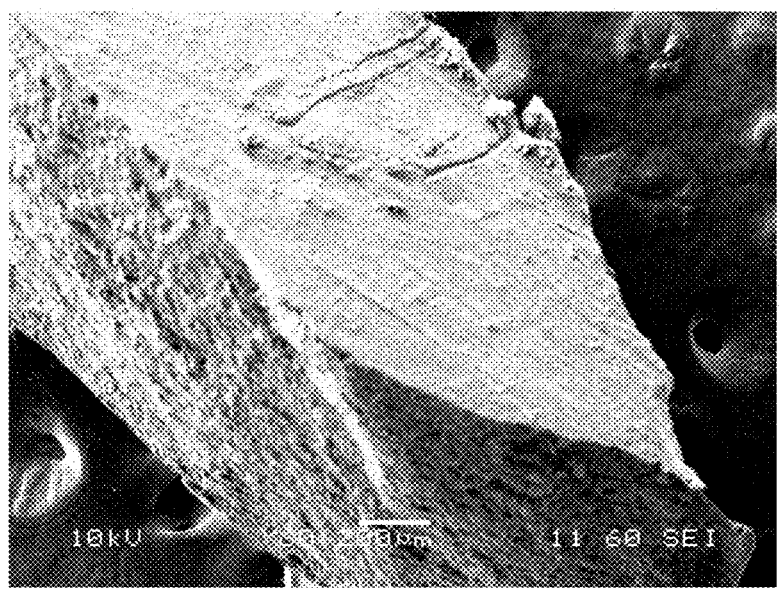
FIG. 10 is a micrograph of TpPa-1 pellet showing the change in morphology of the crystallographically oriented pellet. Scale is indicated.
Figure 13:
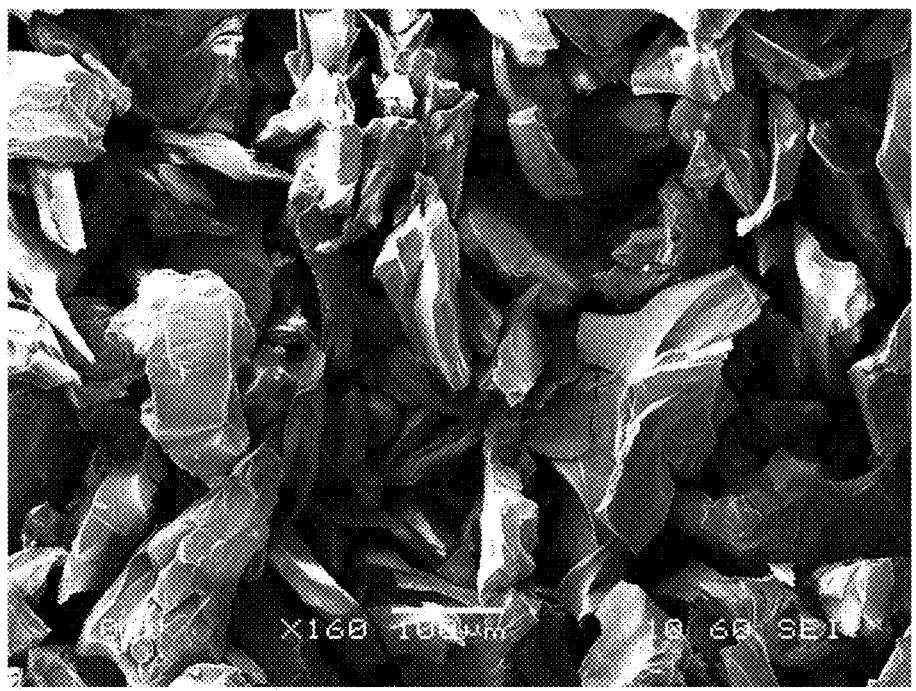
FIG. 13 is a micrograph of CTF-1 powder showing the agglomerated morphology of the microcrystalline powder. Scale is indicated.
Figure 14:
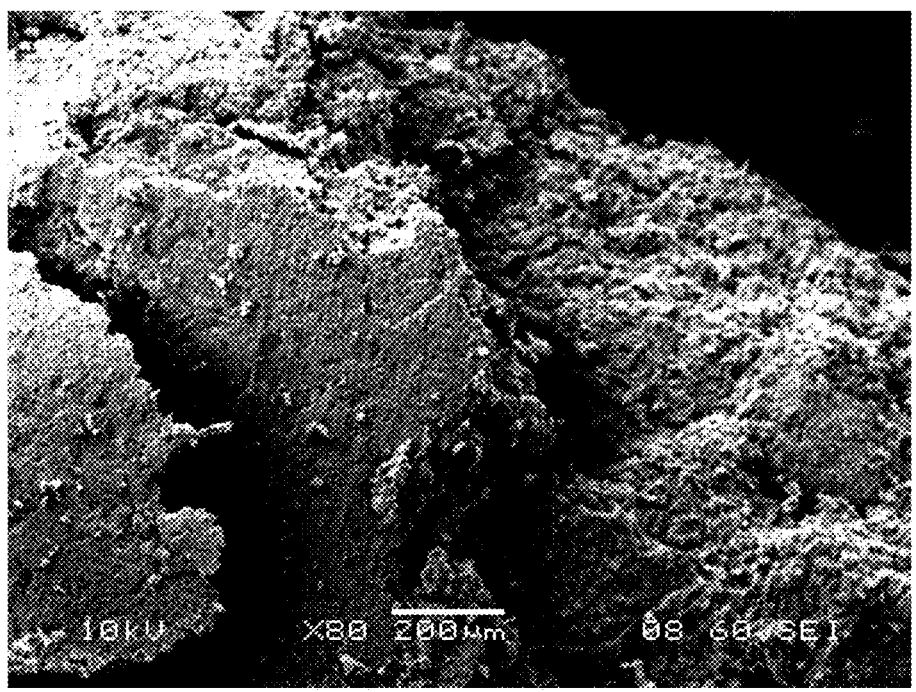
FIG. 14 is a micrograph of TpPa-1 pellet evidencing the change in morphology of the crystallographically oriented pellet. Scale is indicated.

To further observe the dynamic behavior of Li$^+$ within the COF, the $^7$Li static solid-state nuclear magnetic resonance (ssNMR) spectrum of the LiClO$_4$ impregnated COF-5 (powder) was compared to LiClO$_4$(s). FIG. 4C displays the spectrum of the reference compound solid LiClO$_4$ (green), to illustrate the spectroscopic behavior of Li$^+$ in a solid matrix with very limited mobility. A broad signal is observed in the spectrum as a result of solid-state dipole-dipole and quadrupolar couplings between $^7$Li sites. Determination of the $T_1$ relaxation time by saturation-recovery pulse sequence with magic angle spinning, MAS (FIG. 4D) resulted in a $T_1$=2426±131 s. This large value is commensurate with non-mobile $^7$Li$^+$ species in a very restrictive environment, as expected for a non-conducting solid salt. The presence of more mobile $^7$Li species, results in diminishing the effect of the solid-state couplings yielding narrow $^7$Li NMR signals as observed in the LiClO$_4$ impregnated COF-5 (FIG. 4C, purple), compared to solid LiClO$_4$. Saturation recovery experiments resulted in relaxation times of $T_1$=1.91±0.05 s, about 4 orders of magnitude smaller than the solid perchlorate salt. Thus, the presence of sharper signals and much smaller $T_1$ relaxation times evidences dynamic behavior of the Li$^+$ cation in the solid COF implying high ionic mobility within. A question regarding the COF-5 impregnated with LiClO$_4$ is whether the lithium is located within the pores or is bound to the surface. The isotropic $^7$Li MAS NMR spectrum of the lithium treated COF-5 exhibits only a single resonance, indicating the presence of only one environment for $^7$Li. The previously described $T_1$ measurements indicate that $^7$Li$^+$ species in this environment is highly mobile. Taken together, these results are inconsistent with rigidly bound surface lithium and imply that the LiClO$_4$ is located within the pores.

Another question is the effect of the mechanical treatment on the porosity of the materials. It was observed that pressing COF-5 into pellets results in samples that exhibit no porous behavior to N$_2$ gas. It has been shown (Chandra, S. et al. *J. Am. Chem. Soc.* 2013, 135, 17853-17861) that mechanical processing in COFs results in the decrease or loss of porous behavior, as an effect of the disturbance of long-range pore structure due to the sliding of the layers. While not wishing to be bound by theory, it is believed that there is a slow diffusion effect of the N$_2$ into the pellet due to the limited gas accessibility to the pores arising from the mechanical pressing. Impregnation of the COF powder with LiClO$_4$ before mechanical processing results in the isotherm shape and pore size distribution of COF-5 with much less absolute N$_2$ uptake (ca. 7%). This indicates effective impregnation of the Li salt within the COF, as the salt clogs the pores and increases the effective mass of the COF. Once the COF is impregnated, the apparent loss of porosity to gas does not seem to inhibit $Li^+$ conduction. On the other hand, immersion of a non-impregnated COF-5 pellet in the 1 M $LiClO_4$/THF solution results in no Nyquist behavior. In fact such pellets are observed to rapidly return to powder form. Thus impregnation of the COF with Li salts is vital while is still porous, before the mechanical processing.

The $Li^+$-COF clathrate creates a stable long life storage that could be potentially used in energy storage applications. Further efforts on the study Li-ion mobility, elucidation of in-pore vs. grain boundary $Li^+$ mobility, formation of passivation layers, $Li^+$ transport number, and incorporation into battery assemblies are currently ongoing.

It is disclosed herein that pressing 2D COF powders into pellets for device fabrication in solid-state electrolytes, results in an anisotropic crystallographic ordering of the sheets. This crystallographic alignment is a property applicable to 2D COFs of different molecular functionality and crystallographic symmetry. The crystallographically aligned materials display fast Li-ion conductivity and dynamics within the COFs, and exceptional electrochemical stability to lithium.

Specific COFs

The COFs of the disclosure can take any two dimensional framework/structure. For example, using the methods of the disclosure COFs having any of the following RCSR codes (O'Keeffe et al. Acc. Chem. Res. 2008, 41, 1782-1789) can be obtained: bew, bex, bey, car, cem, cem-a, cem-d, esp, esq, fes, fss, fsz, fsz-a, fsz-d, fxt, fxt-a, hca, hca-a, hcb (as bnn or gra), hna, hnb, hnc, hnd, hne, htb, htb-a, hxl, kgd, kgd-a, kgm, kra, krb, krc, krd, kre, krf, krg, krh, krj, krj-d, krk, krl, krm, krn, krq, krr, krs, krt, kru, kru-d, krv, krv-d, krw, krw-d, lbl, mcm, mta, mta-a, mtb, mtb-a, mtc, mtc-a, mtd, mtd-a, mte, mte-a, mtf, mtf-a, mtg, mtg-a, mth, mth-a, ply, pna, pnb, pnc, pnd, pne, pnf, png, pnh, sdb, sdc, sdd, sde, sdf, sdg, sdh, sdi, sdj, sdk, sdl, sdm, sdn, sdo, sdp, sdq, sdr, sdu, sdv, sdw, sdx, sdy, sdz, sql, stz, suz, tdr, tds, tdt, tdu, tdv, tdw, tdx, tdy, tdz, tth, tth-a, usm, usm-d, var. These 2-dimensional framework types can stack as staggered, eclipsed, stepped, serrated, zig-zag, or turbostratic. Examples of COFs that are suitable for uses herein are COF-5, ZnPc-BBa COF, TpPa-1 COF, and CTF-1 COF. COF-5 and ZnPc-BBa COF are synthesized by the boronate condensation of 1,4-phenylene-bis-boronic acid with either 2,3,6,7,10,11-hexahydroxytryphenylene (HHTP) in 1:1 mesitylene/dioxane or 1:1 or zinc 2,3,9,10,16,17,23,24-octahydroxy-phthalocyanine (ZnPc) in 2:1 N,N-dimethyl-acetamide/o-dichlorobenzene. TpPa-1 is synthesized by the Schiff condensation reaction of 1,3,5-triformylphloroglucinol (Tp) with p-phenylenediamine (Pa), for TpPa-1, in acidified 1:1 mesitylene/dioxane. CTF-1 is synthesized by ionothermal trimerization of 1,4-dicyano-benzene in molten $ZnCl_2$.

In specific examples, the COF can be COF-1, COF-5, COF-6, COF-8, COF-10, COF-11 Å, COF-14 Å, COF-16 Å, COF-18 Å, COF-42, COF-43, COF-66, COF-366, TP-COF, NiPc-PBBA COF, CTF-0, CTF-1, HTTP-DBP COF, ZnPc-Py COF, ZnPc-DPB COF, ZnPc-NDI COF, ZnPc-PPE COF, TpPa-1, or TpPa-2, TpPa-$NO_2$, TpBD-$(NO_2)_2$, TpBD-Me2, TpPa-F4, TpBD-OMe2, TpBD, DhaTph COF, TAPB-TFP COF, iPrTAP-TFP, TAPB-TFPB, ILCOF-1, DAAQ-TFP COF, TAPB-PBA COF, HPB COF, HCB COF, $H_2$P-COF, Ph-An-COF, Tp-Azo COF, TP-PirDI COF, Py-Azine COF, CS COF, CuP-SQ COF, CuP-Ph COF, CuP-TFPh COF, Star-COF, CuPc-COF, CoPc-COF, NiPc BTDA COF, ZnP-COF, Ppy-COF, 1-S COF, 1-Se COF, 1-Te COF, T-COF 1, T-COF 2, T-COF 3, T-COF 4, NTU-COF-1, NTU-COF-2, APTES-COF-1, FCTF-1 COF, TRITER-1, TDCOF-5, or BLP-2 COF.

In still further examples, covalent organic frameworks suitable for use herein can contain functional groups such as alkyl chains, oligo and polyethers, fluorinated alkyl chains, glycol diethers (a.ka., glymes) such as poly(ethylene oxide) (PEO), chains containing anionic groups such as sulfonate, carboxylate, imide, or other anionic groups that can balance the charge of any incorporated ions (e.g., Li-ion).

In further examples, the COF's disclosed herein can comprise a lithium salt. Examples of suitable lithium salts included $LiClO_4$, $LiPF_6$, $LiBF_4$, $Li(CF_3SO_3)$, $Li[N(CF_3SO_2)_2]$, $Li[N(CF_3\ CF_2SO_2)_2]$, $LiAsF_6$, LiH, $Li(n-C_4H_5)$, $LiCH_3$, $Li(tert-C_4H_5)$, $Li(C_6H_5)$, and $Li_2CO_3$.

Description of Exemplary Embodiments

In view of the discoveries noted herein, provided herein are method(s) of processing a 2-dimensional covalent organic framework that involves applying pressure to the covalent organic framework along a uniaxial direction of the covalent organic framework. In one example, the pressure is applied by a pellet press. In a specific embodiment the pressure applied is 2 MPa. Alternatively, the pressure applied is at least 10 MPa.

In further embodiments, the linkage of the covalent organic framework is boroxine, Schiff base, triazine, borazine, or boronate.

Moreover, in certain embodiments, the covalent organic framework is COF-1, COF-5, COF-6, COF-8, COF-10, COF-11 Å, COF-14 Å, COF-16 Å, COF-18 Å, COF-42, COF-43, COF-66, COF-366, TP-COF, NiPc-PBBA COF, CTF-0, CTF-1, HTTP-DBP COF, ZnPc-Py COF, ZnPc-DPB COF, ZnPc-NDI COF, ZnPc-PPE COF, TpPa-1, or TpPa-2, TpPa-$NO_2$, TpBD-$(NO_2)_2$, TpBD-Me2, TpPa-F4, TpBD-OMe2, TpBD, DhaTph COF, TAPB-TFP COF, iPrTAP-TFP, TAPB-TFPB, ILCOF-1, DAAQ-TFP COF, TAPB-PBA COF, HPB COF, HCB COF, $H_2$P-COF, Ph-An-COF, Tp-Azo COF, TP-PirDI COF, Py-Azine COF, CS COF, CuP-SQ COF, CuP-Ph COF, CuP-TFPh COF, Star-COF, CuPc-COF, CoPc-COF, NiPc BTDA COF, ZnP-COF, Ppy-COF, 1-S COF, 1-Se COF, 1-Te COF, T-COF 1, T-COF 2, T-COF 3, T-COF 4, NTU-COF-1, NTU-COF-2, APTES-COF-1, FCTF-1 COF, TRITER-1, TDCOF-5, BLP-2 COF, TpTP-H, TpTP-OEt, TpTP-OMEG, TpTP-ODEG, or TpTP-OTEG In certain embodiments, the covalent organic framework has hexagonal symmetry; trigonal symmetry, tetragonal symmetry, rhombohedral symmetry, orthorhombic symmetry, monoclinic symmetry, or triclinic symmetry.

In addition, the covalent organic framework may further comprise a lithium salt. In specific embodiments, covalent organic framework further comprises $LiClO_4$, $LiPF_6$, $LiBF_4$, $Li(CF_3SO_3)$, $Li[N(CF_3SO_2)_2]$, $Li[N(CF_3\ CF_2SO_2)_2]$, $LiAsF_6$, LiH, $Li(n-C_4H_5)$, $LiCH_3$, $Li(tert-C_4H_5)$, $Li(C_6H_5)$, or $Li_2CO_3$, or combinations thereof.

The covalent organic framework may contain functional groups chosen from alkyl chains, oligo- and polyethers, fluorinated alkyl chains, alkyl chains containing anionic groups, alkyl chains containing sulfonate groups, alkyl chains containing carboxylate groups, imides, or anionic group.

In another embodiment, provided is a method of processing a covalent 2-dimensional organic framework, comprising: contacting the covalent organic framework with a lithium salt; and applying pressure to the covalent organic framework along a uniaxial direction of the covalent organic framework.

Another embodiment provided is a covalent organic framework with anisotropic ordering between hk0 and 001 crystallographic planes.

The covalent organic frameworks provided herein have a number of industrial uses. In one example, a battery is provided comprising a covalent organic framework disclosed herein.

Examples

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the purity and yield obtained from the described process.

Example 1: COFs

All starting materials and solvents, unless otherwise specified, were obtained from commercial sources (Aldrich, Fisher, etc.) and used without further purification. All reactions were performed at ambient laboratory conditions, and no precautions were taken to exclude oxygen or atmospheric moisture unless otherwise specified. Anhydrous N,N-dimethylformamide (DMF), Dichloromethane (DCM), and tetrahydrofuran (THF) were purified using a custom-built alumina-column based solvent purification system (INERT). Anhydrous Dioxane, 1,2-dichloroethane (DCE), 1,2-dichlorobenzene (DCB), and acetone were obtained from Aldrich (Sureseal). Triethylamine (TEA) was distilled and stored under $N_2(g)$ from $CaH_2$ into molecular sieves. Deuterated solvents ($CDCl_3$ and DMSO) were obtained from Cambridge Isotope Lab. Mesitylene was dried over activated 4 Å molecular sieves. 1,3,5-triformylphloroglucinol ("TFPG" or "Tp"), 2,3,6,7,10,11-hexahydroxytriphenylene (HHTP), and zinc 2,3,9,10,16,17,23,24-octahydroxy-phthalocyanine (ZnPc) were prepared according to published procedures (Chong, J. H. et al., *J. Org. Lett.* 2003, 5, 3823-3826; Morimoto, K., et al., *Eur. J. Org. Chem.* 2013, 1659-1662; Ivanov, A. V., et al., *Russ. Chem. Bull. Int. Ed.* 2003, 52, 1562-1566).

Pellets were prepared by placing the powders of degassed COF sample in an Arfilled glovebox (MBraun). Ca. 30 mg of COF powder was placed in a custom built die (0.25 in. o.d.) and pressed using a uniaxial pellet press (MTI Corp.) to a pressure of 2, 4, 6, 8, 10 and 12 MPa. The width of each of pellet was measured using a caliper. Powders of COF pellets were recovered by grinding the pellet using an agata mortar and pestle.

Powder X-ray diffraction measurements were performed using a Rigaku Miniflex 600 diffractometer, with θ-2θ Bragg-Brentano geometry, and a 600 W (40 kV, 15 mA) Cu X-ray tube source using $CuK_\alpha$ radiation ($\lambda$=1.5418 Å), samples were measured from 2 to 30 2-theta degrees or 2 to 50 2-theta degrees with a step size of 0.02 degrees and a scan rate of 0.5 s per step. Powder samples were prepared by dropping the powder sample on glass borosilicate slide and gently pressing the powder with a razor blade spatula. Pellets were placed in an aluminum hollow sample holder supported with a strip of tape.

Microwave crystallizations were performed using a CEM Discover LabMate Microwave reactor, using a IntelliVent Attenuator Assembly as the pressure device for the experiments. The vessels used for the crystallizations were the 10-mL thick walled pyrex reaction vessels. The sample vessels were placed in the open vessel attenuator with the spacer and capped with the IntelliVent attenuator for each of the runs. The microwave was set to 250 watts, 175° C., pressure set to 50 psi, and with varying times according to each COF. Linewidth analysis for determination of crystalline size and strain was performed in GSAS-II [Toby, B. H.; Von Dreele, R. B. *J. Appl. Crystallog.* 2013, 46, 544-549] from the unprocessed diffraction patterns. Profile fittings were performed using Le Bail refinements (GSAS-II Peak-Fit) using a Thomson-Cox-Hastings modified pseudo-Voight function with modified Finger-Cox-Jephcoat asymmetry parameter. This function allows for complete decoupling of the instrumental (gaussian) and the sample (lorentzian) broadening parameters. A silicon standard (RS-RP-4327SG) was used to determine the instrumental peak broadening parameters (U, V, W from the gaussian component). Refinement of the ab-direction parameters was obtained from the first four hk0 reflections (100, 110, 200, 210) between 2.0-11.0° (2-theta) from the perpendicular alignment of the pellet; refinements of the c-direction parameters were obtained from the 001 reflection between 21-30° (2-theta) from the parallel alignment of the pellet. First, a background function ($5^{th}$ order Chebyshev polynomial) was manually input (and not refined), and the peak positions and intensities of the reflections of interest were refined. Crystalline strain parameter (Y from the lorentzian component) was refined along with asymmetry, peak positions and intensities; followed by refinement of the domain parameter (X from the lorentzian component) along with asymmetry, peak positions and intensities. The strain parameter was then refined again including asymmetry, peak position, peak intensities, and background; followed by size parameter refinement including asymmetry, peak position, peak intensities, and background. Final refinements included strain and size parameters, asymmetry, peak position, and peak intensities. X and Y parameters, along with their corresponding error (esd) and residuals ($R_{wp}$) were extracted and utilized to estimate the crystalline size (p) and strain (S) with the following formulas:

Crystalline size (p):

$$p = \frac{18000 \cdot K \cdot \lambda}{X \cdot \pi}$$

Crystalline strain (S):

$$S = Y \cdot \frac{\pi}{18000} \cdot 100\%$$

where K is the Scherrer constant (0.90), λ is the wavelength (0.15418 nm), X and Y are the lorentzian component of the peak profile and π=3.14. Fitted parameters are in TABLE 1. Simulated PXRD patterns were calculated using the Reflex module in Materials Studio (v8.0, Biovia) from the CIF file of the respective COF retrieved from their respective publications.

TABLE 1

Particle size and strain of COF-5 from profile fittings.

| Sample | Direction | p (nm) | esd (nm) | S (%) | esd (%) | wRp (%) |
|---|---|---|---|---|---|---|
| powder | ab | 37.522 | 0.529 | 3.933 | 0.193 | 9.16 |
| | c | 6.096 | 0.402 | 0.719 | 0.224 | 10.88 |
| 2 Mpa | ab | 14.587 | 0.117 | 4.834 | 0.405 | 3.49 |
| | c | 3.588 | 0.024 | 6.219 | 0.325 | 1.29 |
| 4 Mpa | ab | 10.927 | 0.066 | 5.585 | 0.572 | 8.04 |
| | c | 5.520 | 0.060 | 14.783 | 0.120 | 1.47 |
| 6 Mpa | ab | 10.507 | 0.082 | 9.881 | 1.233 | 1.63 |
| | c | 8.285 | 0.149 | 19.947 | 0.133 | 1.2 |
| 8 Mpa | ab | 10.779 | 0.254 | 10.810 | 0.935 | 1.29 |
| | c | 8.089 | 0.154 | 20.226 | 0.836 | 1.07 |
| 10 Mpa | ab | 10.678 | 0.128 | 14.912 | 0.411 | 1.76 |
| | c | 2.882 | 0.021 | 21.258 | 0.160 | 1.06 |
| 12 Mpa | ab | 11.881 | 0.135 | 16.770 | 0.359 | 1.75 |
| | c | 2.749 | 0.054 | 25.333 | 0.442 | 1.31 |
| 12 MPa (ground) | ab | 11.238 | 0.213 | 4.281 | 0.607 | 4.25 |
| | c | 1.974 | 0.006 | 0.689 | 0.096 | 0.99 |

Electrochemical impedance spectroscopy was performed inside an Ar filled glovebox using a bipotentiostat-galvanostat (730C CI Instruments, Austin, TX). The 2-electrode cell comprised an asymmetric cell with composition:

Li|COF(LiClO$_4$)|steel

The cell was annealed under Ar at 80° C. for 2 h prior to measurements. Variable temperature was performed under Ar by placing the cell inside a silicone-heating mantle with an electronic temperature controller (BriskHeat, Columbus, OH) and a K-type thermocouple sensor. Complex impedance was measured from $10^0$ to $10^6$ Hz with initial voltage of 0.0 V, and amplitude of 200 mV and quiet time of 1 s. The conductivity of the pellet was determined by the following formula:

$$\sigma = w/AR_e$$

where w is the width of the pellet in cm, A the area in cm$_2$ and $R_e$ the resistance at the electrolyte, which corresponds to the real component (Z) of the impedance at high frequencies.

Solid-state $^7$Li nuclear magnetic resonance was measured on an Agilent DD2 500 MHz narrow-bore spectrometer operating at 194.23307 MHz with an Agilent 5.0 mm T3 probe (Agilent, Santa Clara, CA). A spectral width of 40.3 kHz was employed and 512 complex points were collected. All spectra employed $^1$H decoupling at a frequency of 499.77755 MHz using SPINAL decoupling (Fung, B. M., et al., *J. Magn. Reson.* 2000, 142, 97-101) with a 6.87 μs decoupling pulse. All spectra were externally referenced to the LiClO$_4$ in D$_2$O at 0.00 ppm. Samples were packed in a 5 mm zirconium oxide rotor under Ar atmosphere.

The T$_1$ value of $^7$Li in solid LiClO$_4$ was measured using a saturation recovery pulse sequence with 300 saturation pulses and recovery times varying from 50.0 to 1000.0 s. The spectrum was acquired at a magic angle spinning (MAS) speed of 7.0 kHz and only the isotropic resonances was integrated to obtain of T$_1$ according to the formula:

$$I = I_o[1 - \exp(-t/T_1)]$$

Where I is the resonance peak intensity at time t, I$_o$ is the peak intensity at saturation time and T$_1$ is the spin-lattice relaxation constant.

The T$_1$ of solid $^7$Li in COF-5 (i.e., COF-5 soaked in THF containing LiClO$_4$ and then dried) was also measured with a saturation recovery experiment with 300 saturation pulses and recovery times varying from 1.0 to 60.0 s. All other parameters are as described above for solid LiClO$_4$.

N$_2$ gas adsorption isotherm analysis was performed using a Micromeritics ASAP 2020 porosimetry analyzer. The measurement was performed at 77 K (liquid N$_2$ bath) utilizing degassed and activated samples of COF-5 before and after Li salt impregnation. Pore size distribution plot was obtained from Non-Local Density Functional Theory (NLDFT) fitting of the adsorption isotherm utilizing a cylindrical oxide model for N$_2$ gas. LiClO$_4$—COF-5 showing a decrease in the uptake of N$_2$ while retaining pore size distribution, indicating less accessibility due to guest molecules inside of the pores.

Synthetic Procedures

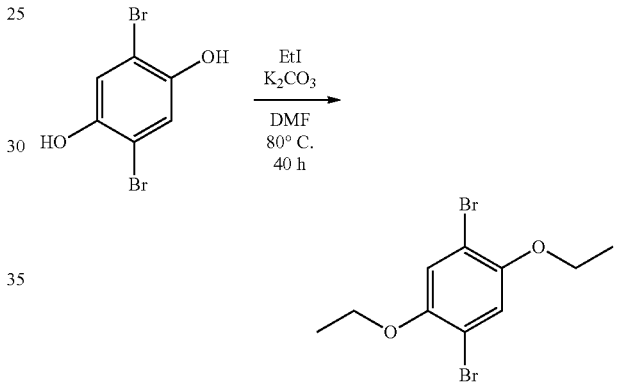

1,4-dibromo-2,5-diethoxybenzene. 2,5-dibromo-hydroquinone (9.0 g, 33.59 mmol), and K$_2$CO$_3$ (27.8 g, 201.5 mmol) were loaded in a 250 mL flame dried Schlenk flask loaded with a magnetic stirrer. The flask was evacuated to a pressure of 150 mtorr and backfilled with N$_2$(g), repeating this purge procedure 3 times. N,N-dimethylformamide (DMF, 135 mL) and iodoethane (5.95 mL, 11.56 g, 73.4 mmol) were added to the flask dropwise under N$_2$(g). The solution was stirred at room temperature for 4 h and then heated to 80° C. with stirring for 40 h. The reaction was cooled to room temperature and quenched with aqueous 1 M HCl (100 mL), and stored at 4° C. for 12 h. A crystalline white solid was obtained and purified by filtration using a medium porosity glass frit funnel, rinsed with cold H$_2$O and dried under vacuum. Yield. 10.10 g (92.8%). Characterized via $^1$H NMR and $^{13}$C NMR.

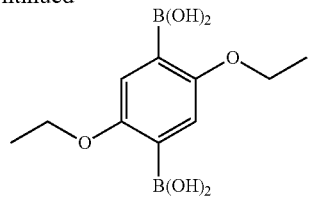

2,5-diethoxy-1,4-phenylene-diboronic acid. 1,4-dibromo-2,5-diethoxybenzene (2.0 g, 6.2 mmol) was loaded in a flame-dried 100 mL Shlenk flask loaded with a magnetic stirrer. The flask was evacuated to a pressure of 150 mtorr and backfilled with N$_2$ (g), repeating this purge procedure 3 times. Anhydrous tetrahydrofuran (THF, 50 mL) was added under N$_2$ (g) via syringe, and the mixture was cooled to −78° C. using a dry ice/acetone bath. n-Butyl lithium (5.6 mL 2.5 M in hexanes, 14.2 mmol) was added dropwise under N$_2$(g) at −78° C. over the course of 10 min, and the mixture was stirred for 2 h. Triisopropyl borate (4.27 mL, 3.48 g, 18.52 mmol) was added dropwise. The reaction was stirred for 12 h allowing it to warm to room temperature after which it was quenched with aqueous 1 M HCl (60 mL) forming a white precipitate in a clear solution. The mixture was concentrated at 40° C. under vacuum in a rotary evaporator to remove the THF. The white solid was isolated by filtration, rinsed with H$_2$O, and dried under vacuum for 12 h resulting in a white off solid. Yield: 1.46 g (93.2%). Characterized via $^1$H NMR and $^{13}$C NMR.

Figure 15:
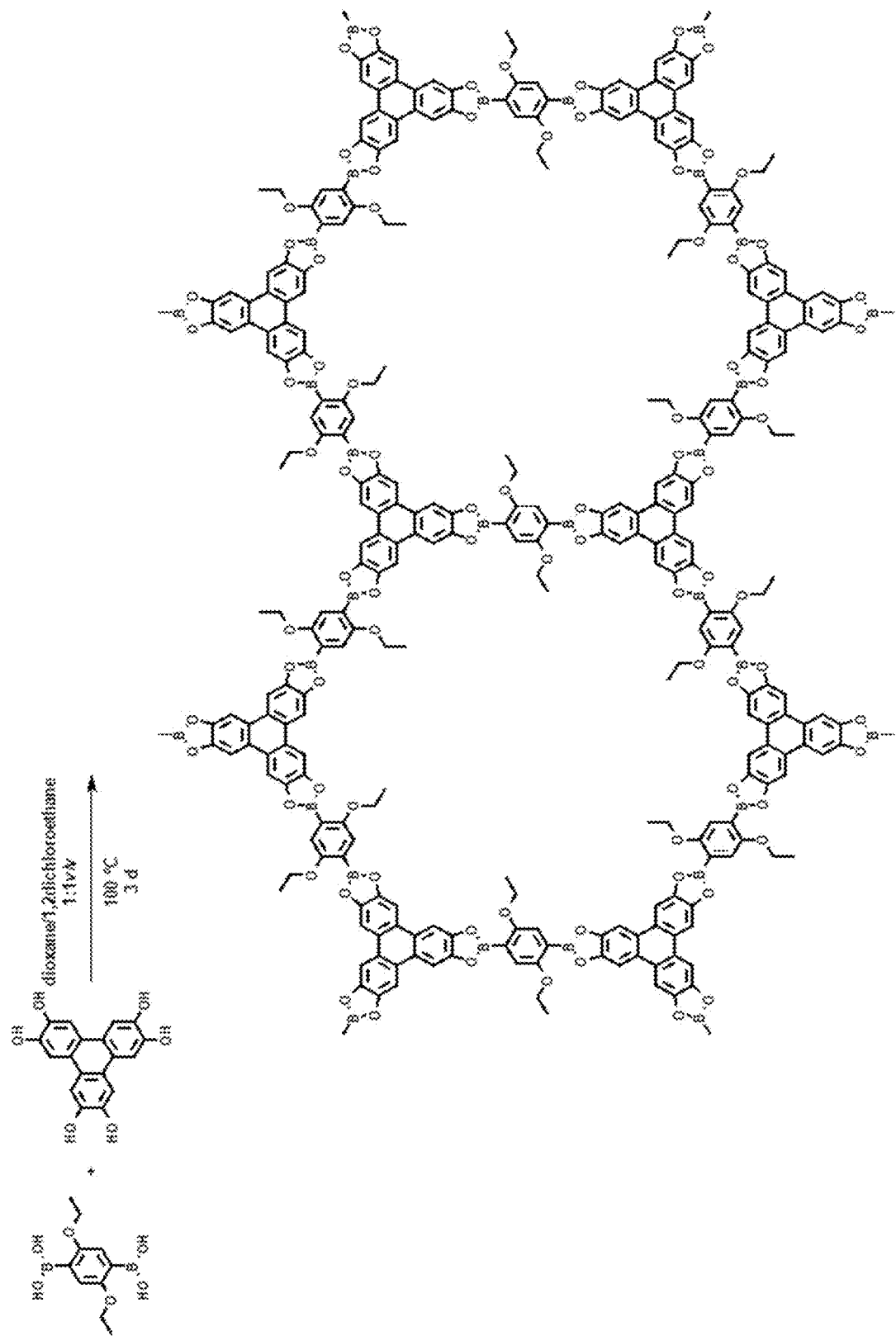
FIG. 15 scheme for synthesizing COF-5-(EtO)$_2$.

COF-5-(EtO)$_2$ (FIG. 15). 2,5-diethoxy-1,4-phenylene-diboronic acid (0.020 g, 0.0614 mmol) and 2,3,6,7,10,11-hexahydroxytriphenylene (HHTP, 0.031 g, 0.123 mmol), and dioxane/1,2-dichloroethane solution (1 mL, 1:1 v/v) were loaded in a borosilicate tube, flash frozen under liquid N$_2$, evacuated to 150 mtorr, and sealed with a propane torch. The sealed tube was immersed in a sonication bath for 20 min and placed in an isothermal oven at 100° C. for 72 h. After removing from the oven, the tube was opened, after which the formed black solid was separated by vacuum filtration using a 0.45 μm nylon filter paper (GE HLS). The obtained solid was rinsed with anhydrous THF (3×2 mL), and immersed in anhydrous THF for 3 d, exchanging the solvent 5 times during this period. The remaining solvent was removed by decantation, and the solvent-wet powder was placed in a 15 mL round bottom flask with a Schlenk valve adaptor and evacuated under dynamic vacuum to 10 mtorr using a Schlenk line for 12 h at 80° C. Yield: 18 mg (36%). The degassed powder was stored in an Ar filled glove box. Product was characterized via Powder X-ray Diffraction.

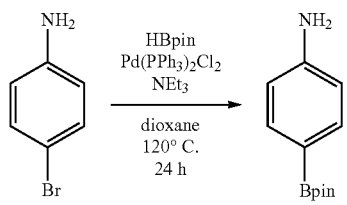

4-amino-phenyl-boronic acid pinacol ester. 4-bromoaniline (5.38 g, 31.25 mmol), PdCl$_2$(PPh$_3$)$_2$, triethylamine (17.4 mL, 125 mmol), and 1,4-dioxane (60 mL) were loaded in a 250 mL Schlenk flask loaded with a magnetic stirrer. The mixture was flash frozen in liquid N$_2$, evacuated to an internal pressure of 50 mtorr, and allowed to thaw under static vacuum. The freeze/pump/thaw procedure was repeated 3 more times, after which 4,4,5,5-tetramethyl-1,3,2-dioxaborolane (13.6 mL, 93.8 mmol) was added dropwise slowly over the course of 10 min. Under N$_2$(g) flow, a water cooled condenser was attached with a bubbler and a positive N$_2$(g) flow at the top. The reaction mixture was heated to 120° C. for 24 h. The reaction mixture was cooled to room temperature, quenched with H$_2$O (80 mL), extracted with CH$_2$Cl$_2$ (3×50 mL) and the combined organic extracts were rinsed with H$_2$O (3×50 mL), brine (3×50 mL), dried over anhydrous Na$_2$SO$_4$(s) and filtered over celite. Activated charcoal (ca. 2 g) was added to the dried extract, heated to 45° C., stirred for 15 min, and hot filtered over a pluf of siliga gel. Removal of the solvent at 40° C. under vacuum in a rotary evaporator afforded a yellow solid. Yield: 1.03 g (36%). Characterized via proton ($^1$H) and $^{13}$C NMR.

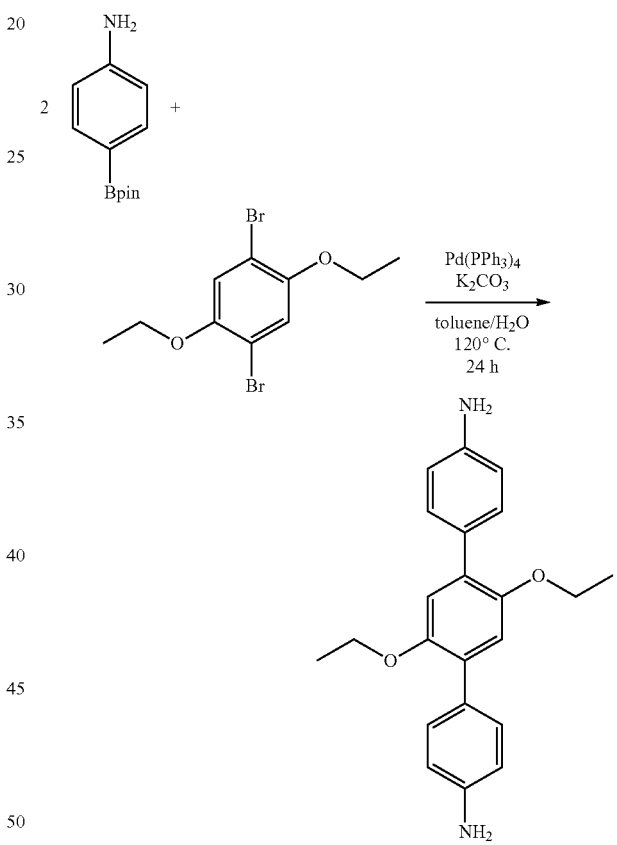

Synthesis of 1,4-bis(4-aminophenyl)-2,5-diethoxy-benzene (monomer A). 1,4-dibromo-2,5-diethoxy-benzene (0.100 g, 0.309 mmol), 4-amino-phenyl-boronic acid pinacol ester (0.170 g, 0.772 mmol), Pd(PPh$_3$)$_4$(0.050 g, 0.031 mmol), K$_2$CO$_3$ (0.640 g, 4.64 mmol), H$_2$O (1 mL), toluene (1 mL) were loaded in a 50 mL Schlenk flask loaded with a magnetic stirrer. The mixture was flash frozen in liquid N$_2$, evacuated to an internal pressure of 50 mtorr, and allowed to thaw under static vacuum. The freeze/pump/thaw procedure was repeated 3 more times, after which a water cooled condenser was attached with a bubbler and a positive N$_2$(g) flow at the top. The reaction mixture was heated to 120° C. for 24 h under N$_2$(g). The reaction mixture was cooled to room temperature, quenched with H$_2$O (5 mL), extracted with CH$_2$Cl$_2$ (3×10 mL) and the combined organic extracts were rinsed with $H_2O$ (3×10 mL), brine (3×10 mL), dried over anhydrous $Na_2SO_4$(s) and filtered over celite. Removal of the solvent at 40° C. under vacuum in a rotary evaporator followed by column chromatography ($SiO_2$, 30% EtOAc in hexanes) afforded an off white solid. Yield: 0.040 g (37%). Characterized with proton (1H), $^{13}C$ NMR and HRMS.

Figure 16:
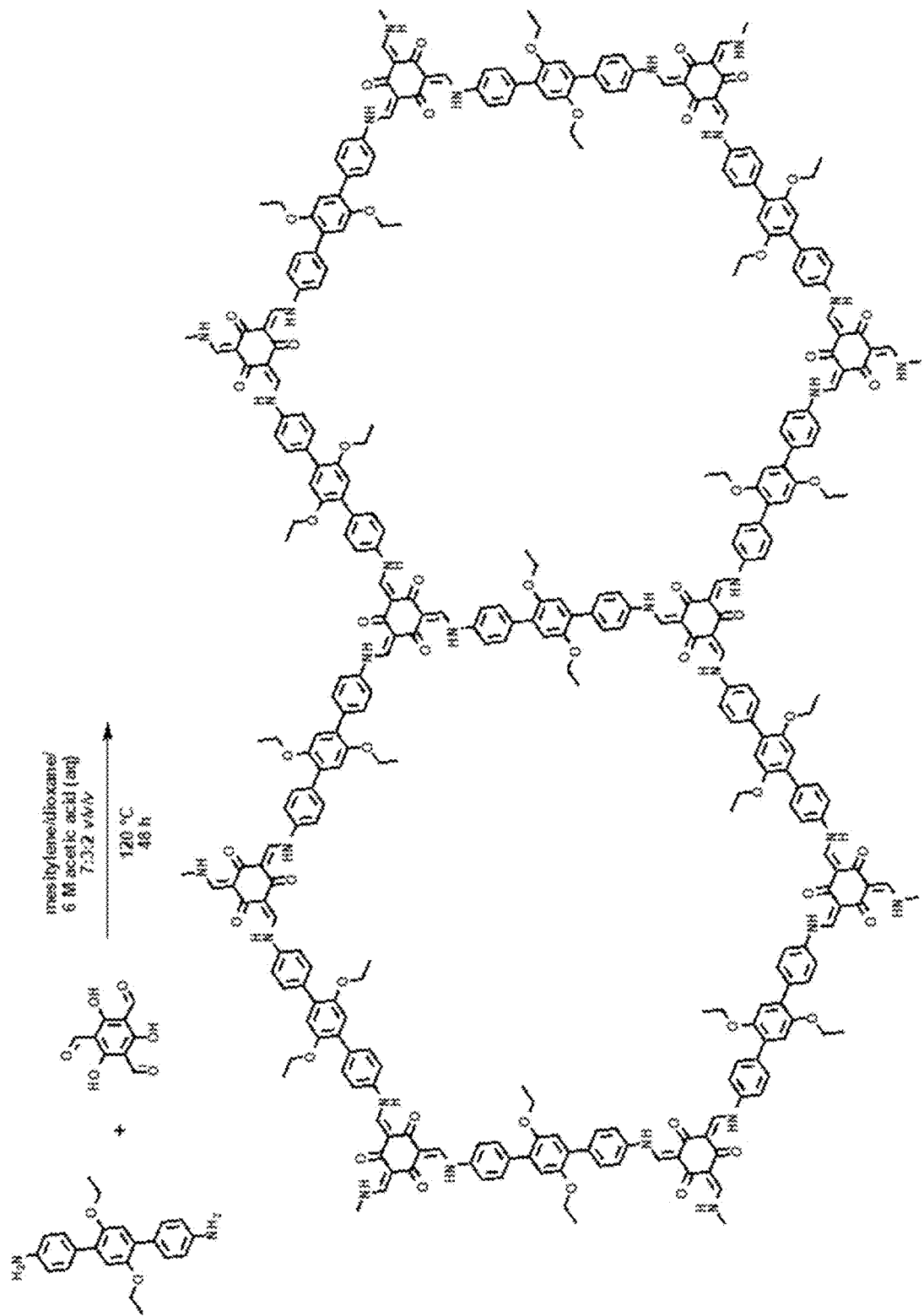
FIG. 16 is a diagram showing a scheme for synthesizing terphenyl-diethoxy-Enamine COF.

Synthesis of terphenyl-diethoxy-Enamine COF (FIG. 16). The COF was made via solvothermal synthesis by charging a borosilicate tube, with one end sealed, with the monomer A (0.034 g, 0.1 mol) and TFPG (0.014 g, 0.067 mol). After which, the addition of 1 mL a mesitylene/dioxane/aqueous 6 M acetic acid solution (7:3:2 v/v/v) was added and the mixture was sonicated for 30 min and then vortex for another 30 min. Then the tube was flash frozen and evacuated to 150 mtorr and flame sealed under static vacuum. The tube was placed in a sand bath and in an isothermal oven at 120° C. for 48 h. Mustard yellow solid was obtained, which was purified by filtration and rinsed with 60 mL of anhydrous THF. The obtained bright yellow solid was then immersed in anhydrous THF for 24 h, replacing the solvent three times during this period. The solid was purified by filtration and heated to 90° C. at 10 mtorr for 24 h. Yield: 40 (82%). Product was characterized via Powder X-ray diffraction.

COF-1. Adapted from Côté et al. (*Science* 2005, 310, 1166-1170) 1,4-phenylene-diboronic acid (120 mg, 0.78 mmol), mesitylene (6.0 mL) and anhydrous Dioxane (6.0 mL) were added in a 20 mL PTFE digestion cup with a stainless steel jacket (Parr), and tightly capped. The mixture was gently stirred and placed in an isothermal oven at 120° C. for 48 h. After removing from the oven, the bomb was allowed to cool to room temperature, after which the obtained white solid was separated by vacuum filtration using a 0.45 μm nylon filter paper (GE HLS). The obtained solid was rinsed with anhydrous THF (2×20 mL), and immersed in anhydrous THF for 2 d, exchanging the solvent 5 times during this period. The remaining solvent was removed by decantation, and the solvent-wet powder was placed in a 15 mL round bottom flask with a Schlenk valve adaptor and evacuated under dynamic vacuum to 10 mtorr using a Schlenk line for 12 h at 80° C. Yield: 98 mg (89%). The degassed powders were stored in an Ar filled glove box.

COF-5. Adapted from Côté et al. (Id.) 1,4-phenylene diboronic acid (129 mg, 0.780 mmol), HHTP (149 mg, 0.457 mmol), Mesitylene (4.0 mL) and anhydrous Dioxane (4.0 mL) were added in a 20 mL PTFE digestion cup with a stainless steel jacket (Parr), and tightly capped. The mixture was gently stirred and placed in an isothermal oven at 100° C. for 72 h. After removing from the oven, the bomb was allowed to cool to room temperature, after which the obtained white solid was separated by vacuum filtration using a 0.45 μm nylon filter paper (GE HLS). The obtained solid was rinsed with anhydrous THF (2×20 mL), and immersed in anhydrous THF for 2 d, exchanging the solvent 5 times during this period. The remaining solvent was removed by decantation, and the solvent-wet powder was placed in a 15 mL round bottom flask with a Schlenk valve adaptor and evacuated under dynamic vacuum to 10 mtorr using a Schlenk line for 12 h at 80° C. Yield: 112 mg (36%). The degassed powder was stored in an Ar filled glove box.

TpPa-1. Adapted from Banerjee et al. (*J. Am. Chem. Soc.* 2012, 134, 19524-19527). TFPG (200 mg, 0.952 mmol), p-phenylenediamine (154 mg, 1.43 mmol), anhydrous dioxane (16.0 mL), and 2.1 mL of 6 M acetic acid (aq) were added in a 20 mL PTFE digestion cup with a stainless steel jacket (Parr), and tightly capped. The mixture was gently stirred and placed in an isothermal oven at 100° C. for 72 h. After removing from the oven, the bomb was allowed to cool to room temperature, after which the obtained white solid was separated by vacuum filtration using a 0.45 μm nylon filter paper (GE HLS). The obtained solid was rinsed with anhydrous THF (2×20 mL), and immersed in anhydrous THF for 2 d, exchanging the solvent 5 times during this period. The remaining solvent was removed by decantation, and the solvent-wet powder was placed in a 15 mL round bottom flask with a Schlenk valve adaptor and evacuated under dynamic vacuum to 10 mtorr using a Schlenk line for 12 h at 80° C. Yield: 180 mg (74%). The degassed powder was stored in an Ar filled glove box.

CTF-1. Adapted from Kuhn et al. (*Angew. Chem. Int. Ed.*, 2008, 47, 3450-3453) 1,4-dicyanobenzene (1.0 g, 7.80 mmol) and $ZnCl_2$ (0.94 g, 6.90 mmol) were loaded in a quartz tube, and the tube was evacuated to 150 mtorr and sealed with a propane torch. The tube was heated to 400° C. for 40 h. The tube was opened and the obtained black powder was recovered and rinsed with 1.0 M HCl (aq) and water (3×100 mL), the powder was dried and heated to 400° C. under dynamic vacuum (10 mtorr) for 5 h to remove remaining $ZnCl_2$. Yield: 620 mg (62%). In preparation for the pellet, the CTF-1 powder was ground in a mortar and pestle with a few drops of isopropyl alcohol to make a paste. To ca. 50 mg of CTF-1, nafion solution (250 μL 5 wt % in EtOH) was added and additional grinding was performed using a mortar and pestle. The CTF/nafion composite was allowed to fully dry and evacuated under dynamic vacuum to 10 mtorr using a Schlenk line for 12 h at room temperature and stored in an Ar filled glove box.

ZnPc-BBA COF. Adapted from Colson et al. (*J. Polym. Sci. Part A: Polym. Chem.*, 2015, 53, 378-384) 1,4-phenylene diboronic acid (14.5 mg, 0.06 mmol), ZnPc (21.0 mg, 0.03 mmol), N,N-dimethylacetamide/o-dichlorobenzene (2 mL, 2:1 v/v) were loaded in a borosilicate tube, flash frozen under liquid $N_2$, evacuated to 150 mtorr, and sealed with a propane torch. The sealed tube was immersed in a sonication bath for 20 min and placed in an isothermal oven at 120° C. for 72 h. After removing from the oven, the tube was opened, after which the obtained white solid was separated by vacuum filtration using a 0.45 μm nylon filter paper (GE HLS). The obtained solid was rinsed with anhydrous toluene (2 mL), and immersed in anhydrous toluene for 1 d, exchanging the solvent 5 times during this period. The remaining solvent was removed by decantation, and the solvent-wet powder was placed in a 15 mL round bottom flask with a Schlenk valve adaptor and evacuated under dynamic vacuum to 10 mtorr using a Schlenk line for 12 h at 80° C. Yield: 21 mg (79%). The degassed powder was stored in an Ar filled glove box.

Poly(ethylene oxide) (PEO) based materials are widely considered as promising candidates of polymer hosts in solid-state electrolytes for high energy density secondary lithium batteries. Unfortunately, because of the high crystallinity of the ethylene oxide (EO) chains, which can restrain the ionic transition it has insufficient ionic conductivity. Efforts to address this deficiency, including blending, modifying and making PEO derivatives, are ongoing (Z. Xue et al., *J. Mater. Chem. A*, 3, 19218-19253 (2015)). COF's modified with chelating pendants groups, such as glyme oligo-ethylene oxide (PEO) pendant, that complex period table group 1 metal ions (e.g., Li ions) is disclosed. As with the other COF's, the Li ions in these PEO-COF's are highly mobile and show substantially increased conductivity.

Compound S1. 4-bromoaniline (2.00 g, 12.0 mmol), Pd(PPh$_3$)$_2$Cl$_2$ (0.300 g, 1.20 mmol), triethylamine (6.5 mL, 46.5 mmol), and 1,4-dioxane (45 mL) were loaded in a 250 mL Schlenk flask loaded with a magnetic stirrer. The mixture was bubbled with N$_2$(g) for 20 min, after which 4,4,5,5-tetramethyl-1,3,2-dioxaborolane (5.1 mL, 34.9 mmol) was added dropwise under N$_2$(g) over the course of 10 min observing mild gas evolution. Under N$_2$(g) flow, a water cooled condenser was attached to the top of the flask and a rubber septum and a bubbler and N$_2$(g) inlet at the top.

The reaction mixture was heated to 120° C. for 12 h followed by TLC. The reaction mixture was cooled to room temperature, quenched with water (80 mL), extracted with EtOAc (3×50 mL) and the combined organic extracts were rinsed with water (3×50 mL), brine (3×50 mL), dried over anhydrous Na$_2$SO$_4$(s) and filtered over celite. Activated charcoal (ca. 2 g) was added to the organic extract, heated to 45° C., stirred for 15 min, and hot filtered over a plug of silica gel. Removal of the solvent at 40° C. under reduced pressure in a rotary evaporator afforded a yellow solid. Yield: 2.4 g (90%). $^1$H NMR (400 MHz, CDCl$_3$, 25° C.) δ 7.65-7.58 (d, 1H), 6.69-6.63 (d, 1H), 3.83 (s, 1H), 1.32 (s, 6H). $^{13}$C NMR (100 MHz, CDCl$_3$) δ 149.61, 136.76, 114.42, 83.63, 77.04, 25.20.

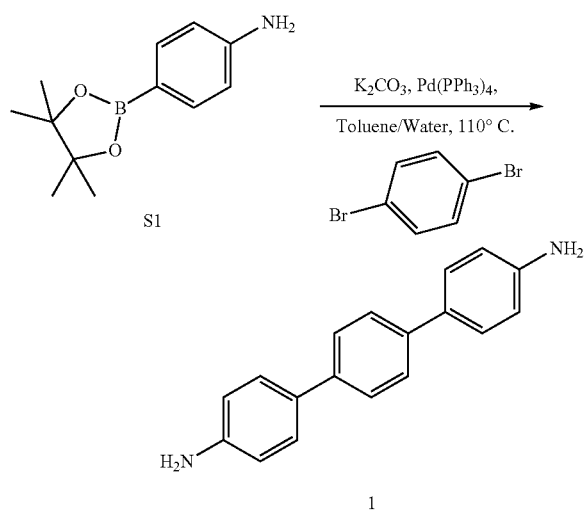

Monomer 1. 1,4-dibromobenzene (0.980 g, 4.15 mmol), S1 (2.0 g, 9.13 mmol), Pd(PPh$_3$)$_4$(0.3 g, 0.415 mmol), K$_2$CO$_3$ (8.6 g, 62.3 mmol), water (10 mL), toluene (10 mL) were loaded in a 50 mL Schlenk flask loaded with a magnetic stirrer. The mixture was flash frozen in liquid N$_2$, evacuated to an internal pressure of 50 mtorr, and allowed to thaw under static vacuum. The freeze/pump/thaw procedure was repeated three more times, after which the flask was backfilled with N$_2$(g) and under N$_2$ flow a water cooled condenser was attached with a red septum, bubbler and a positive N$_2$(g) flow at the top. The reaction mixture was heated to 120° C. for 24 h under N$_2$(g), tracked by TLC. The reaction mixture was cooled to room temperature, quenched with water (5 mL), extracted with EtOAc (3×10 mL) and the combined organic extracts were rinsed with water (3×10 mL), brine (3×10 mL), dried over anhydrous Na$_2$SO$_4$(s) and filtered through celite. Removal of the solvent at 40° C. under reduced pressure in a rotary evaporator followed by column chromatography (SiO$_2$, 45% EtOAc in hexanes) afforded a white solid. Yield: 0.560 g (52%). $^1$H NMR (400 MHz, DMSO-d$_6$) δ 7.53 (s, 1H), 7.39-7.35 (d, 1H), 6.66-6.62 (d, 1H), 5.20 (s, 1H). $^{13}$C NMR (100 MHz, DMSO) δ 148.18, 137.93, 127.11, 126.82, 125.55, 114.22, 99.51, 39.52. HRMS (ESI-TOF) m/z calculated for C$_{18}$H$_{16}$N$_2$ [M+H]$^+$: 261.1393, found 261.1355.

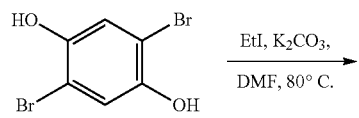

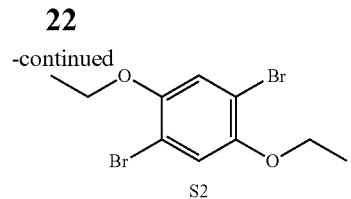

Compound S2. 2,5-dibromo-hydroquinone (9.0 g, 33.59 mmol), and K$_2$CO$_3$ (27.8 g, 201.5 mmol) were loaded in a 250 mL flame dried Schlenk flask loaded with a magnetic stirrer. The flask was evacuated to a pressure of 150 mtorr and backfilled with N$_2$(g), purge procedure three times. Anhydrous DMF (135 mL) and iodoethane (5.95 mL, 11.56 g, 73.4 mmol) were added to the flask dropwise under N$_2$(g). The solution was stirred at room temperature for 4 h at room temperature and then heated to 80° C. with stirring for 40 h followed by TLC. The reaction was cooled to room temperature and quenched with aqueous 1 M HCl (100 mL), and stored at 4° C. for 12 h. A crystalline white solid was formed and purified by filtration using a medium porosity glass frit funnel, rinsed with cold water and dried under vacuum at room temperature. Yield 10.10 g (93%). $^1$H NMR (400 MHz, DMSO-d$_6$) δ 7.33 (s, 1H), 4.05 (q, J=7.0 Hz, 2H), 1.34-1.28 (m, 3H). $^{13}$C NMR (100 MHz, CDCl3) δ 150.16, 118.82, 111.35, 77.16, 66.11, 14.90.

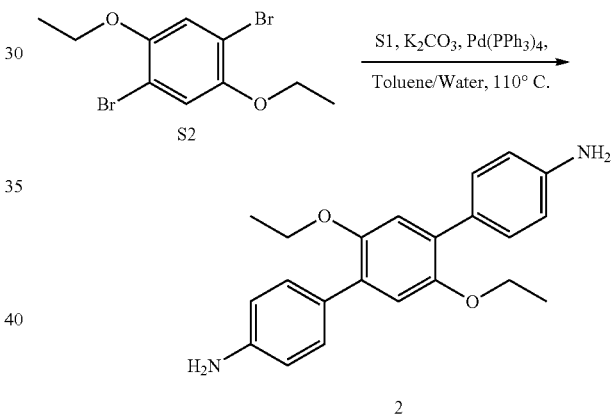

Monomer 2. S2 (0.309 mmol), S1 (0.772 mmol), Pd(PPh3)4 (0.031 mmol), K2CO3 (4.64 mmol), water (1 mL), toluene (1 mL) were loaded in a 50 mL Schlenk flask loaded with a magnetic stirrer. The mixture was flash frozen in liquid N$_2$, evacuated to an internal pressure of 50 mtorr, and allowed to thaw under static vacuum. The freeze/pump/thaw procedure was repeated three more times, after which the flask was backfilled with N$_2$(g) and under N$_2$ flow a water cooled condenser was attached with a red septum, bubbler and a positive N$_2$(g) flow at the top. The reaction mixture was heated to 120° C. for 24 h under N$_2$(g), tracked by TLC. The reaction mixture was cooled to room temperature, quenched with water (5 mL), extracted with EtOAc (3×10 mL) and the combined organic extracts were rinsed with water (3×10 mL), brine (3×10 mL), dried over anhydrous Na$_2$SO$_4$(s) and filtered through diatomaceous earth (a.k.a., celite). Removal of the solvent at 40° C. under vacuum in a rotary evaporator followed by column chromatography (SiO$_2$, 45% EtOAc in hexanes) afforded an off pale/white solid. Yield: 0.040 g (37%). $^1$H NMR (400 MHz, CDCl$_3$) δ 7.46-7.40 (d, 2H), 6.94 (s, 1H), 6.78-6.69 (d, 2H), 3.97 (q, J=7.0 Hz, 2H), 3.71 (s, 2H), 1.31 (t, J=7.0 Hz, 3H).

$^{13}$C NMR (100 MHz, DMSO) δ 149.50, 147.54, 129.67, 129.18, 125.40, 115.39, 113.39, 99.51, 73.50, 64.33, 39.52. HRMS (ESI-TOF) m/z calculated for $C_{22}H_{25}N_2O_2$ [M+H]$^+$: 349.1916, found 349.1893.

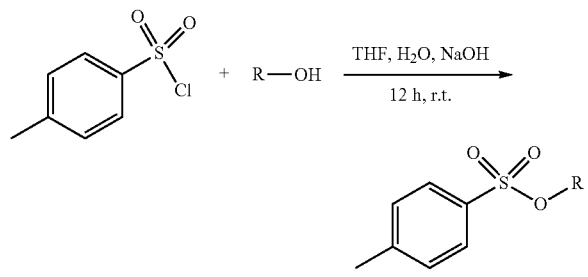

General Procedure for S3a-c. Three separate flasks were prepared; flask 1 was composed of p-toluenesulfonylchloride (TsCl) (237.0 mmol) dissolved in THF (74 mL), flask 2 had NaOH (367.0 mmol) dissolved in H$_2$O (74 mL), flask 3 was composed of the alcohol (131.0 mmol) dissolved in THF (74 mL). Flask 2 and 3 were combined and then to an addition funnel flask 3 was added to it and placed over the flask 2 and 3 mixture to be added dropwise for 12h at room temperature, tracked by TLC. The reaction was quenched with water (100 mL) and extracted with DCM (2×60 mL) dried over anhydrous Na$_2$SO$_4$(s) and filtered through celite. The organic layer was reduced under pressure to afford a clear oil.

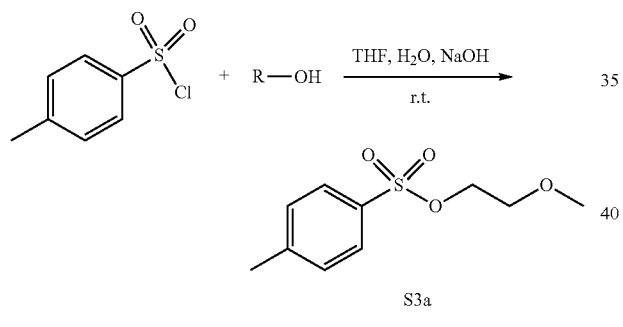

Compound S3a. Yield 20.08 g (87.0%). $^1$H NMR (400 MHz, CDCl3) δ 7.82-7.77 (d, 1H), 7.36-7.31 (d, 1H), 4.17-4.12 (m, 1H), 3.60-3.53 (m, 1H), 2.44 (s, J=0.4 Hz, 2H). $^{13}$C NMR (100 MHz, CDCl$_3$) δ 145.18, 133.32, 130.17, 128.31, 70.27, 69.42, 59.36, 22.00. HRMS (ESI-TOF) m/z calculated for $C_{10}H_{15}O_4S$ [M+H]$^+$: 231.0691, found 231.0663.

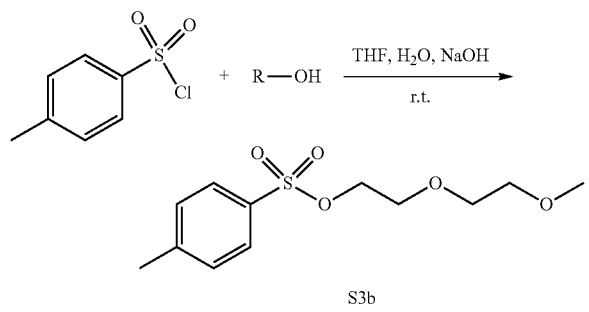

Compound S3b. Yield 19.08 g (84.0%). $^1$H NMR (400 MHz, Chloroform-d) δ 7.82-7.76 (d, 1H), 7.36-7.31 (d, 1H), 4.19-4.14 (m, 1H), 3.70-3.65 (m, 1H), 3.59-3.55 (m, 1H), 3.49-3.44 (m, 1H), 2.44 (s, J=0.3 Hz, 2H). $^{13}$C NMR (100 MHz, CDCl$_3$) δ 145.15, 133.32, 130.15, 128.34, 72.15, 71.03, 69.57, 69.06, 59.40, 21.99. HRMS (ESI-TOF) m/z calculated for $C_{12}H_{19}O_5S$ [M+H]$^+$: 275.0953, found 275.0959.

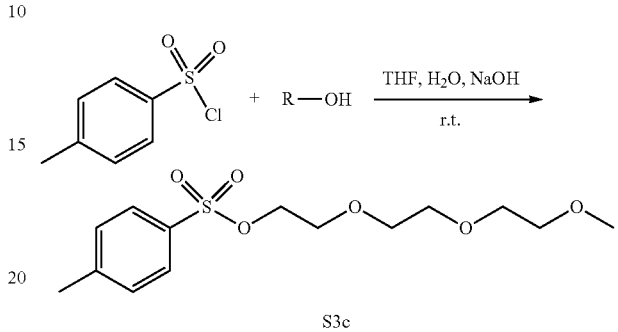

Compound S3c. Yield 6.50 g (33.0%). 1H NMR (400 MHz, CDCl3-d) δ 7.85 (d, J=8.3 Hz, 1H), 7.39 (d, J=7.9 Hz, 1H), 4.23-4.19 (m, 1H), 3.80 (t, J=6.7 Hz, 1H), 3.76-3.72 (m, 1H), 3.68-3.63 (m, 3H), 3.60-3.56 (m, 1H), 3.42 (s, 1H). $^{13}$C NMR (100 MHz, CDCl$_3$) δ 144.90, 133.15, 129.93, 128.10, 77.16, 72.03, 70.87, 70.69, 70.67, 69.35, 68.80, 68.10, 59.15, 25.74, 21.76. HRMS (ESI-TOF) m/z calculated for $C_{14}H_{23}O_6S$ [M+H]$^+$: 319.1215, found 319.1220.

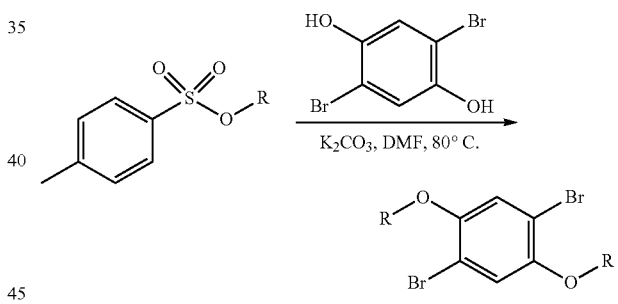

General procedure for S4a-c. 2,5-dibromo-hydroquinone (0.747 mmol), S3a-c (1.87 mmol), and K$_2$CO$_3$ (4.48 mmol) were loaded in a 50 mL flame dried Schlenk flask loaded with a magnetic stirrer. The flask was evacuated to a pressure of 150 mtorr and backfilled with N$_2$(g), repeating this purge procedure 3 times. Anhydrous DMF (4 mL) was added to the flask under N$_2$(g). The solution was stirred and heated to 80° C. with stirring for 12 h and tracked by TLC. The reaction was cooled to room temperature and quenched with water (20 mL) and a precipitant was formed. A crystalline white solid was obtained and purified by filtration using a medium porosity glass frit funnel, rinsed with water and dried under vacuum.

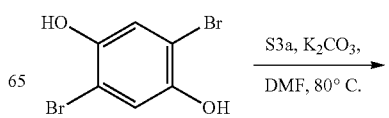

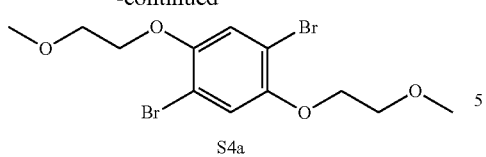

S4a

Compound S4a. Using S3a. Yield 0.280 g (89.0%). $^1$H NMR (400 MHz, Acetonitrile-d3) δ=7.26 (s, 1H), 4.13-4.08 (m, 2H), 3.72-3.66 (m, 2H), 3.37 (s, 3H). $^{13}$C NMR (100 MHz, CDCl3) δ 150.54, 119.43, 111.66, 77.16, 71.01, 70.27, 59.58.

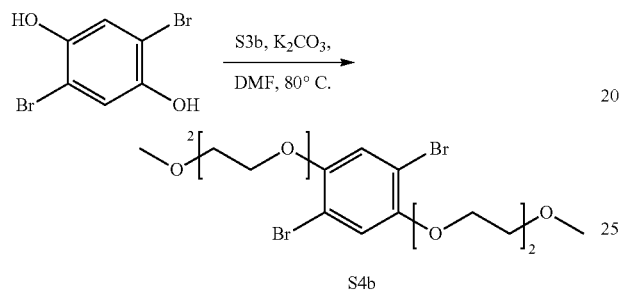

S4b

Compound S4b. Using S3b. Yield 0.240 g (60.0%). $^1$H NMR (500 MHz, Acetonitrile-$d_3$) δ 7.30-7.27 (s, 1H), 4.11 (td, J=4.5, 2.0 Hz, 3H), 3.78 (dtd, J=5.8, 2.8, 1.2 Hz, 2H), 3.64 (ddd, J=6.1, 3.1, 1.1 Hz, 2H), 3.51-3.46 (m, 2H), 3.32-3.28 (s, 3H). $^{13}$C NMR (100 MHz, CDCl$_3$) δ 150.46, 119.52, 119.32, 111.52, 77.16, 72.16, 71.14, 70.41, 70.38, 69.73, 59.24. HRMS (ESI-TOF) m/z calculated for $C_{16}H_{25}Br_2O_6$ [M+H]$^+$: 472.9997, found 472.9995.

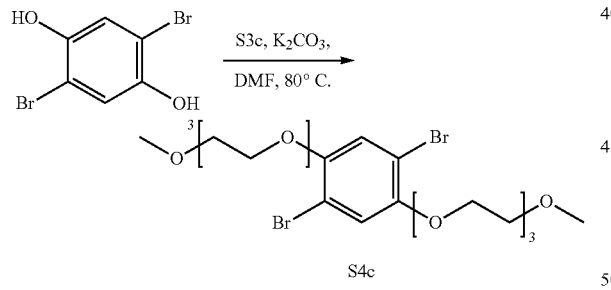

S4c

Compound S4c. Using S3c. Yield 4.9 g (70.0%). $^1$H NMR (400 MHz, CDCl$_3$) δ 7.09 (s, 1H), 4.10-4.04 (m, 2H), 3.83-3.78 (m, 2H), 3.73-3.68 (m, 2H), 3.64-3.58 (m, 4H), 3.52-3.46 (m, 2H), 3.32 (s, 3H). $^{13}$C NMR (100 MHz, CDCl$_3$) δ 162.59, 150.39, 119.23, 111.44, 77.16, 72.03, 71.17, 70.81, 70.67, 70.28, 69.66, 59.12, 36.56, 31.50, 14.28. HRMS (ESI-TOF) m/z calculated for $C_{20}H_{33}Br_2O_8$ [M+H]$^+$: 561.0522, found 561.0519.

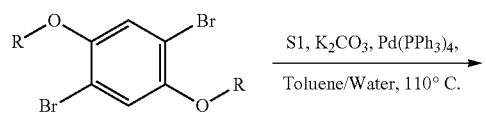

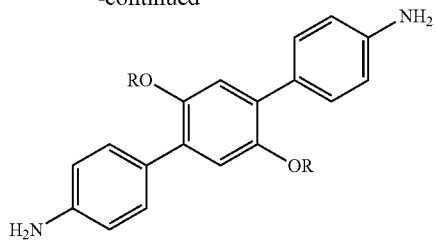

General Procedure for 3a-c. S3a-c (0.309 mmol), S1 (0.772 mmol), Pd(PPh3)4 (0.031 mmol), $K_2CO_3$ (4.64 mmol), water (1 mL), toluene (1 mL) were loaded in a 50 mL Schlenk flask loaded with a magnetic stirrer. The mixture was flash frozen in liquid $N_2$, evacuated to an internal pressure of 50 mtorr, and allowed to thaw under static vacuum. The freeze/pump/thaw procedure was repeated three more times, after which the flask was backfilled with $N_2$(g) and under $N_2$ flow a water cooled condenser was attached with a red septum, bubbler and a positive $N_2$(g) flow at the top. The reaction mixture was heated to 120° C. for 24 h under $N_2$(g), tracked by TLC. The reaction mixture was cooled to room temperature, quenched with water (5 mL), extracted with EtOAc (3×10 mL) and the combined organic extracts were rinsed with water (3×10 mL), brine (3×10 mL), dried over anhydrous $Na_2SO_4$(s) and filtered through celite. Removal of the solvent at 40° C. under reduced pressure in a rotary evaporator followed by column chromatography (SiO$_2$, 45% EtOAc in hexanes) afforded a tan solid.

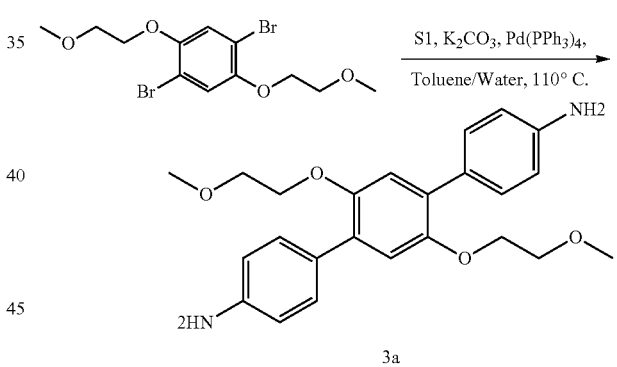

3a

Monomer 3a. With S4a removal of the solvent at 40° C. under vacuum in a rotary evaporator followed by column chromatography (SiO$_2$, 75% EtOAc in hexanes) afforded an off tan solid. Yield: 0.360 g (36%). $^1$H NMR (400 MHz, DMSO-d$_6$) δ 7.33-7.28 (m, 2H), 6.88 (s, 1H), 6.61-6.55 (m, 2H), 5.11 (s, 2H), 4.06-4.00 (m, 2H), 3.59 (dd, J=3.8, 2.2 Hz, 2H), 3.27 (s, 3H). $^{13}$C NMR (100 MHz, DMSO) δ 149.62, 147.60, 129.76, 129.11, 128.89, 128.19, 125.20, 115.33, 113.36, 70.68, 68.26, 58.21, 39.52. HRMS (ESI-TOF) m/z calculated for $C_{24}H_{29}N_2O_4$ [M+H]$^+$: 409.2127, found 409.2120.

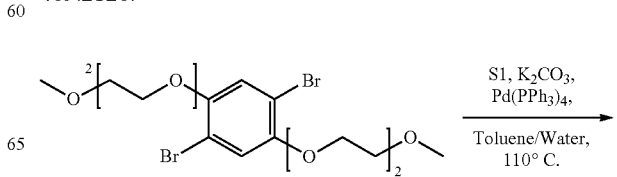

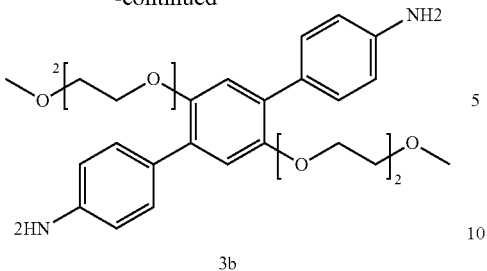

3b

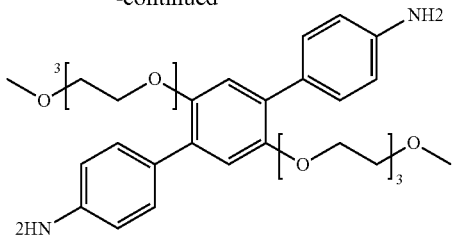

3c

Monomer 3b. With S4b removal of the solvent at 40° C. under vacuum in a rotary evaporator followed by column chromatography (SiO$_2$, neat EtOAc) afforded an off tan/yellow solid. Yield: 0.850 g (42%). $^1$H NMR (400 MHz, DMSO-d$_6$) δ 7.35-7.29 (m, 2H), 6.89 (s, 1H), 6.60-6.55 (m, 2H), 5.12 (s, 2H), 4.03 (dd, J=5.6, 3.8 Hz, 2H), 3.69-3.64 (m, 2H), 3.56-3.52 (m, 2H), 3.45-3.41 (m, 2H), 3.23 (s, 3H). $^{13}$C NMR (100 MHz, DMSO) δ 149.59, 147.59, 129.78, 129.07, 125.19, 115.28, 113.34, 71.32, 71.25, 69.92, 69.83, 69.70, 69.60, 69.16, 68.42, 58.09, 58.02, 40.15, 39.94, 39.73, 39.52, 39.52, 39.31, 39.10, 38.90.

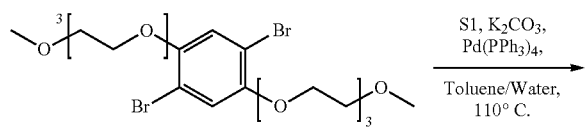

Monomer 3c. With S4c removal of the solvent at 40° C. under vacuum in a rotary evaporator followed by column chromatography (SiO$_2$, 15% MeCN/EtOAc) afforded an off tan/brown solid. Yield: 0.600 g (18%). $^1$H NMR (500 MHz, DMSO-d6) δ=7.35-7.29 (d, 2H), 6.88 (s, 1H), 6.61-6.55 (d, 2H), 5.11 (s, 2H), 4.06-4.00 (m, 2H), 3.69-3.63 (m, 2H), 3.55-3.47 (m, 6H), 3.42-3.38 (m, 2H), 3.22 (s, 3H). $^{13}$C NMR (100 MHz, DMSO) δ 149.58, 147.59, 129.78, 129.07, 125.20, 115.28, 113.34, 71.25, 69.92, 69.84, 69.60, 69.16, 68.43, 58.02, 40.15, 39.94, 39.73, 39.52, 39.31, 39.10, 38.90.

Figure 17:
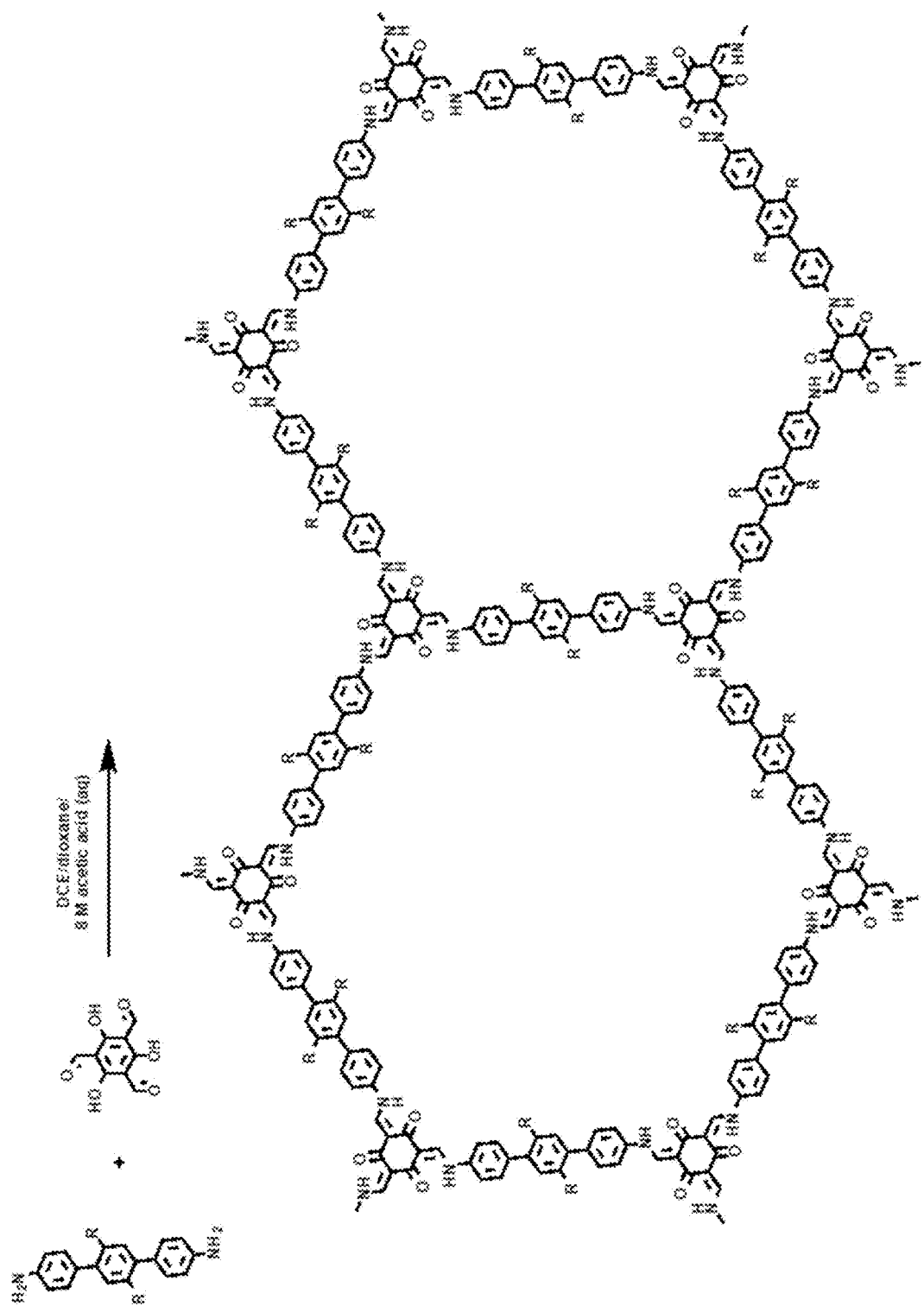
FIG. 17 is a diagram showing a scheme for synthesizing COFs with oligo-ethylene oxide pendant groups.

General Scheme for Preparation of COFs with oligo-ethylene oxide pendant groups also provided in FIG. 17.

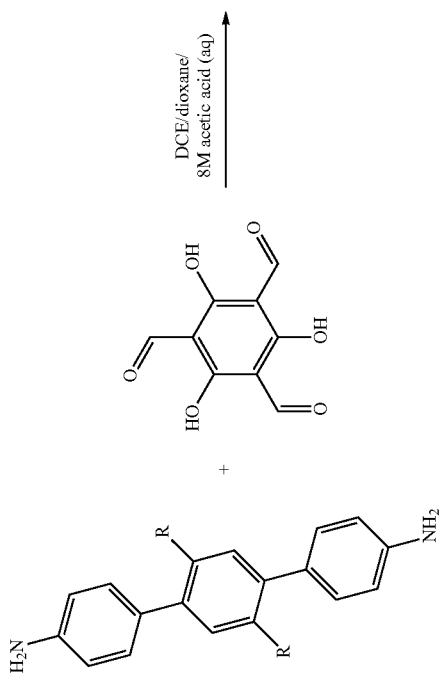

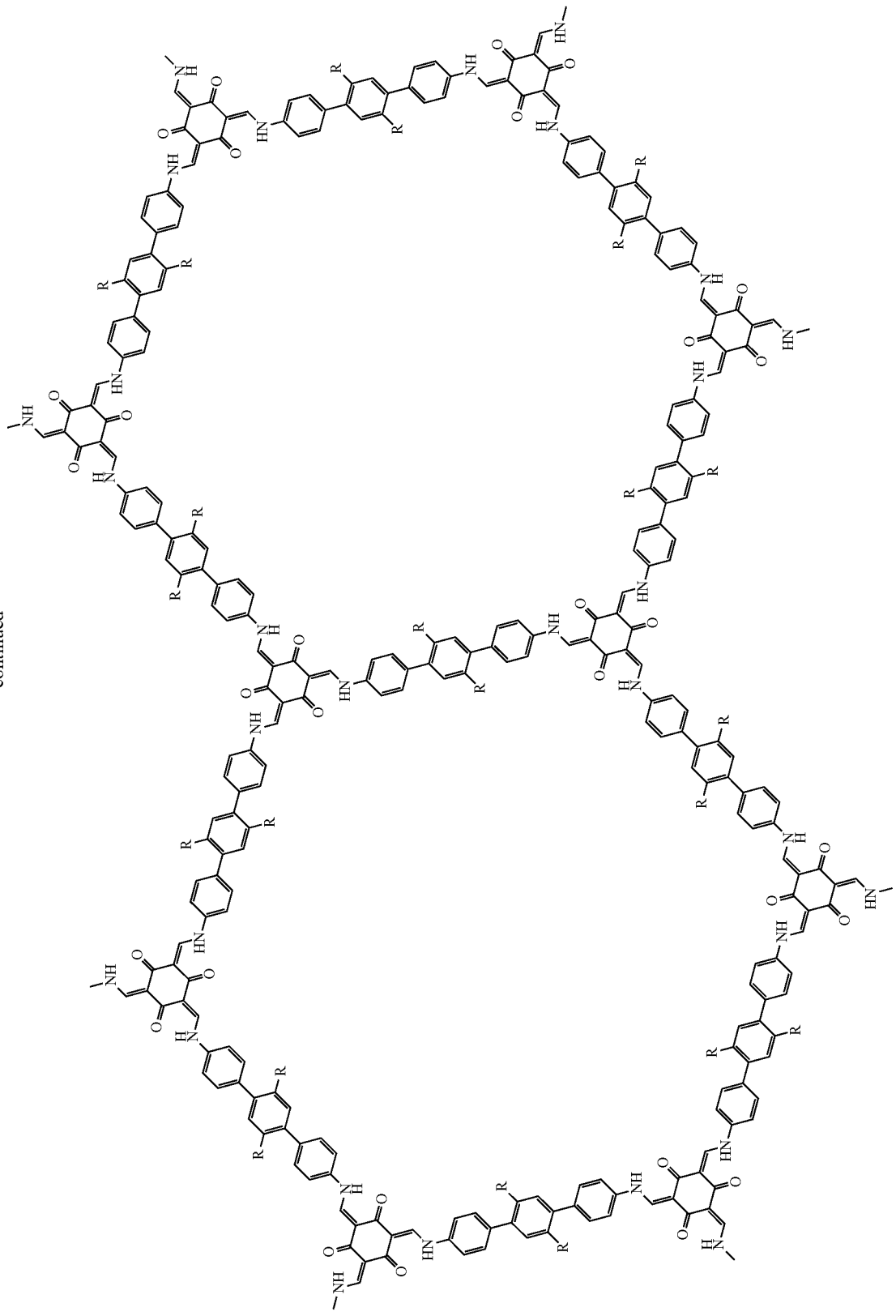

TABLE 2

Compendium of Exemplary COFs with oligo-ethylene oxide pendant groups.

| R= | Name of COF |
|---|---|
| H | TpTP-H |
| $OCH_2CH_3$ | TpTP-OEt |
| $O(CH_2CH_2O)CH_3$ | TpTP-OMEG |
| $O(CH_2CH_2O)_2CH_3$ | TpTP-ODEG |
| $O(CH_2CH_2O)_3CH_3$ | TpTP-OTEG |

Synthesis of terphenyl-COF TpTP-H COF. Monomer 1 (0.020 g, 0.0714 mol) and Tp (0.010 g, 0.0476 mol) were loaded in the microwave pyrex reaction vessel. After which, the addition of 3.1 mL a dichloroethane/dioxane/aqueous 8 M acetic acid solution (1:1:3 v/v/v) was added and the mixture was sonicated for 5 min. Then the tube was placed in the microwave with settings of 250 w, 175° C., for 15 mins. Mustard yellow solid was obtained, which was purified by filtration and rinsed with 10-15 mL of acetone. The obtained yellow/brown solid was then immersed in anhydrous acetone for 24-72 h, replacing the solvent three times per day during this period. The solid was purified by filtration and heated to 120° C. at 6 mtorr for 12 h. Yield: 0.025 g (83%). Product was characterized via Powder X-ray diffraction.

TpTP-OEt COF. Monomer 2 (0.025 g, 0.0714 mol) and Tp (0.010 g, 0.0476 mol) were loaded in the microwave pyrex reaction vessel. After which, the addition of 3.1 mL a DCB/n-propanol/aqueous 8 M acetic acid solution (1:1:3 v/v/v) was added and the mixture was sonicated for 5 min. Then the tube was placed in the microwave with settings of 250 w, 175° C., for 15 mins. Mustard yellow solid was obtained, which was purified by filtration and rinsed with 10-15 mL of acetone. The obtained yellow/brown solid was then immersed in anhydrous acetone for 24-72 h, replacing the solvent three times per day during this period. The solid was purified by filtration and heated to 120° C. at 6 mtorr for 12 h. Yield: 0.030 g (85%). Product was characterized via Powder X-ray diffraction.

TpTP-OMEG COF. Monomer 3a (0.030 g, 0.0714 mol) and Tp (0.010 g, 0.0476 mol) were loaded in the microwave pyrex reaction vessel. After which, the addition of 3.1 mL a DCE/dioxane/aqueous 8 M acetic acid solution (1:1:3 v/v/v) was added and the mixture was sonicated for 5 min. Then the tube was placed in the microwave with settings of 250 w, 175° C., for 45 mins. Mustard yellow solid was obtained, which was purified by filtration and rinsed with 10-15 mL of acetone. The obtained yellow/brown solid was then immersed in anhydrous acetone for 24-72 h, replacing the solvent three times per day during this period. The solid was purified by filtration and heated to 120° C. at 6 mtorr for 12 h. Yield: 0.030 g (75%). Product was characterized via Powder X-ray diffraction.

TpTP-ODEG COF. Monomer 3b (0.040 g, 0.0714 mol) and Tp (0.010 g, 0.0476 mol) were loaded in the microwave pyrex reaction vessel. After which, the addition of 3.1 mL a DCB/n-propanol/aqueous 6 M acetic acid solution (1:1:3 v/v/v) was added and the mixture was sonicated for 5 min. Then the tube was placed in the microwave with settings of 250 w, 175° C., for 15 mins. Mustard yellow solid was obtained, which was purified by filtration and rinsed with 10-15 mL of acetone. The obtained brown solid was then immersed in anhydrous acetone for 24-72 h, replacing the solvent three times per day during this period. The solid was purified by filtration and heated to 120° C. at 6 mtorr for 12 h. Yield: 0.030 g (60%). Product was characterized via Powder X-ray diffraction.

TpTP-OTEG COF. Monomer 3c (0.045 g, 0.0714 mol) and Tp (0.010 g, 0.0476 mol) were loaded in the microwave pyrex reaction vessel. After which, the addition of 3.1 mL a DCB/n-propanol/aqueous 6 M acetic acid solution (1:1:3 v/v/v) was added and the mixture was sonicated for 5 min. Then the tube was placed in the microwave with settings of 250 w, 175° C., for 15 mins. Mustard yellow solid was obtained, which was purified by filtration and rinsed with 10-15 mL of acetone. The obtained brown solid was then immersed in anhydrous acetone for 24-72 h, replacing the solvent three times per day during this period. The solid was purified by filtration and heated to 100° C. at 6 mtorr for 12 h. Yield: 0.023 g (41%). Product was characterized via Powder X-ray diffraction.

Lithium perchlorate impregnation. Degassed COF powder was immersed in 3 mL of 1.0 M $LiClO_4$ in THF solution under Ar for 3 d. Powders were recovered by vacuum filtration and rinsed with anhydrous THF. The Li-impregnated COF was evacuated to 10 mtorr for 8 h at room temperature. The dry powder were pressed into pellets.

Mechanical Processing. Pellets were prepared by placing the powders of degassed COF sample in an Ar-filled glovebox (MBraun). About 40 mg of COF powder was placed in a custom built die (0.25 in diameter) and pressed using a uniaxial pellet press (MTI Corp.) to a pressure of 4 MPa. The width of each of the pellets was measured with a caliper. Powders of COF pellets were recovered by grinding the pellet using a mortar and pistil.

Preparation of $LiClO_4$ Impregnated Powder, Pellet Pressing and Electrochemical Impedance Spectroscopy Activated COF powder was placed in an Ar-filled glovebox. The COF powder (0.050 g) was immersed in a 4 mL of 1.0 M $LiClO_4$ in THF solution and allowed to soak for 72 to 96 hr. After soaking, the powder was recovered by filtration and rinsed with 10 mL of THF. The powder was then placed in a round bottom flask and evacuated to 10 mtorr under dynamic vacuum for 12 h. The dry powder (0.050 g) was pressed into a pellet (0.25 in diameter, A=0.316 $cm^2$) using a Pellet Press (MTI Corp.) at a hydrostatic pressure of 4.0 MPa for 20 min. Elemental analysis. COF-5: $BC_9H_4O_2$ $(LiClO_4)_{0.0377}(THF)_x$: C 56.65%, H 4.50% B 2.89%, Li 0.07%. B:Li molar ratio 1:0.0377. The thickness of the pellet (w) was measured using a caliper. The pellet was placed in a 2 electrode cell consisting of Li|$LiClO_4$(COF-5)|steel with Li as working electrode and steel as counter/reference electrode The cell was annealed under Ar at 80° C. for 2 h prior to measurements. Variable temperature was performed under Ar by placing the cell inside a silicone-heating mantle with an electronic temperature controller (BriskHeat) and a K-type thermocouple sensor. The AC Electrochemical impedance spectrum (EIS) was measured utilizing a potentiostat-galvanostat (730C CI Instruments) from $10^0$ to $10^6$ Hz, with an initial potential of 0.0 V and amplitude of 200 mV and a quiet time of 1 s. The measurement resulted in a typical Nyquist plot, from which the real component of the complex impedance at high frequency corresponds to the resistance of the electrolyte, Re. Ionic conductivity was obtained by the following formula:

$$\sigma = \frac{w}{A \cdot R_e}$$

where σ is the ionic conductivity in S cm$^{-1}$, w is thickness of the pellet in cm, A the area in cm$^2$, and $R_e$ is the resistance of the electrolyte in ohm.

TABLE 3

Ionic conductivities at 25° C.

| COFs | Conductivity σ (mS cm$^{-1}$) |
| --- | --- |
| terphenyl-diethoxy-Enamine COF | 0.590 |
| COF-5[2] | 0.260 |
| TpPa-1 COF[2] | 0.150 |
| COF-5-OEt$_2$ | 0.023 |

The devices, methods and compositions of the appended claims are not limited in scope by the specific methods and compositions described herein, which are intended as illustrations of a few aspects of the claims and any methods and compositions that are functionally equivalent are within the scope of this disclosure. Various modifications of the methods and compositions in addition to those shown and described herein are intended to fall within the scope of the appended claims. Further, while only certain representative methods, compositions, and aspects of these methods and compositions are specifically described, other methods and compositions and combinations of various features of the methods and compositions are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

The disclosures of the references cited herein are provided in their entirety to the extent they are not inconsistent with the teachings herein.

What is claimed is:

1. A compressed 2-dimensional covalent organic framework (COF) comprising crystallographically aligned sheets and pores impregnated with a lithium salt, wherein the COF comprises Li$^+$ conduction, and wherein the covalent organic framework contains functional groups chosen from alkyl chains, oligo- and polyethers, fluorinated alkyl chains, alkyl chains containing anionic groups, alkyl chains containing sulfonate groups, alkyl chains containing carboxylate groups, imides, or anionic group, wherein the covalent organic framework comprises anisotropic ordering between hk0 and 00l crystallographic planes.

2. The covalent organic framework of claim 1, wherein the covalent organic framework comprises a linkage selected from boroxine, Schiff base, triazine, borazine, or boronate.

3. The covalent organic framework of claim 1, wherein the covalent organic framework comprises COF-1, COF-5, COF-6, COF-8, COF-10, COF-11 Å, COF-14 Å, COF-16 Å, COF-18 Å, COF-42, COF-43, COF-66, COF-366, TP-COF, NiPc-PBBA COF, CTF-0, CTF-1, HTTP-DBP COF, ZnPc-Py COF, ZnPc-DPB COF, ZnPc-NDI COF, ZnPc-PPE COF, TpPa-1, or TpPa-2, TpPa-NO$_2$, TpBD-(NO$_2$)$_2$, TpBD-Me2, TpPa-F4, TpBD-OMe2, TpBD, DhaTph COF, TAPB-TFP COF, iPrTAP-TFP, TAPB-TFPB, ILCOF-1, DAAQ-TFP COF, TAPB-PBA COF, HPB COF, HCB COF, H$_2$P-COF, Ph-An-COF, Tp-Azo COF, TP-PirDI COF, Py-Azine COF, CS COF, CuP-SQ COF, CuP-Ph COF, CuP-TFPh COF, Star-COF, CuPc-COF, CoPc-COF, NiPc BTDA COF, ZnP-COF, Ppy-COF, 1-S COF, 1-Se COF, 1-Te COF, T-COF 1, T-COF 2, T-COF 3, T-COF 4, NTU-COF-1, NTU-COF-2, APTES-COF-1, FCTF-1 COF, TRITER-1, TDCOF-5, BLP-2 COF, TpTP-H, TpTP-OEt, TpTP-OMEG, TpTP-ODEG, or TpTP-OTEG or a combination thereof.

4. The covalent organic framework of claim 1, wherein the covalent organic framework has hexagonal symmetry, trigonal symmetry, tetragonal symmetry, rhombohedral symmetry, monoclinic symmetry, or triclinic symmetry.

5. A battery comprising the covalent organic framework of claim 1.

* * * * *